United States Patent [19]
Seki et al.

[11] 3,998,816
[45] Dec. 21, 1976

[54] 7-[5-N-(n-BUTOXYETHOXY CARBONYL AND 2-CHLOROETHOXY CARBONYL)-AMINO] CEPHALOSPORINS C

[75] Inventors: Shigeo Seki, Tokyo; Toshiyasu Ishimaru, Suita, both of Japan

[73] Assignee: Meiji Seika Kaisha, Ltd., Tokyo, Japan

[22] Filed: Apr. 2, 1974

[21] Appl. No.: 457,280

[30] Foreign Application Priority Data

| Apr. 16, 1973 | Japan | 48-42129 |
| May 12, 1973 | Japan | 48-521116 |
| Nov. 29, 1973 | Japan | 48-133012 |
| Nov. 29, 1973 | Japan | 48-133013 |
| Nov. 29, 1973 | Japan | 48-133014 |
| Nov. 29, 1973 | Japan | 48-133015 |
| Dec. 28, 1973 | Japan | 49-144641 |
| Dec. 28, 1973 | Japan | 49-144642 |
| Dec. 28, 1973 | Japan | 49-144643 |
| Dec. 28, 1973 | Japan | 49-144644 |

[52] U.S. Cl. .................. 260/243 C; 424/246
[51] Int. Cl.$^2$ ........................ C07D 501/60
[58] Field of Search .................. 260/243 C

[56] References Cited
UNITED STATES PATENTS 3,124,576   3/1964   Stedman ............... 260/243 C Primary Examiner—Nicholas S. Rizzo
Assistant Examiner—Jose Tovar
Attorney, Agent, or Firm—Larson, Taylor and Hinds

[57] ABSTRACT

New and useful cephem compounds derived from cephalosporin C are provided by this invention, which are valuable as intermediate for the synthesis of another bacteriocidally active cephem derivatives and which are readily extractable from its aqueous solution by means of an organic solvent and enable the cephalosporin C content in the aqueous fermentation broth filtrate to be recovered at an improved yield. Cephalosporin C present in the fermentation broth may be converted into the cephem compounds of this invention by reacting with a substituted chloroformate compound within said filtrate, and the cephem compounds so formed may then be extracted therefrom with an organic solvent. The cephem compounds of this invention further may be converted into a 7-acylamidocephalosporanic acid or 7-aminocephalosporanic acid through some successive reactions.

2 Claims, No Drawings

7-[5-N-(N-BUTOXYETHOXY CARBONYL AND 2-CHLOROETHOXY CARBONYL)-AMINO] CEPHALOSPORINS C

This invention relates to novel and useful cephem derivatives and a method for the preparation of these cephem derivatives. This invention further relates to a process of recovering cephalosporin C in an improved yield from an aqueous solution thereof.

It is known that cephalosporin C is a very useful antibiotic as a raw material for the preparation of other cephem derivative and is produced by culturing a microorganism *Cephalosporium acremonium* in a liquid culture medium and recovering said antibiotic from the fermentation broth containing it. The fermentation broth so obtained usually contains a very low concentration of order of about 0.2 – 0.5% by weight of cephalosporin C. The recovery of cephalosporin C from the fermentation broth has hitherto been conducted by various methods but all the prior art methods previously known are able to recover cephalosporin C from its aqueous solution such as the fermentation broth filtrate only in a commercially unsatisfactorily low yield. This is mainly due to that cephalosporin C is an amphoteric compound which contains one free amino group and two free carboxyl groups in its molecule, so that it is practically difficult to make the cephalosporin C molecule adsorbed by any ion-exchange resin preferentially from its aqueous solution (the fermentation broth) and to elute the cephalosporin C molecule chromatographically out of the ion-exchange resin bearing the cephalosporin C molecule once adsorbed therein. Besides, cephalosporin C is hardly soluble in any organic solvent, although it is soluble in water owing to its amphoteric nature. Accordingly, cephalosporin C can only be recovered from the fermentation broth in an extremely low yield when it is tried to extract the fermentation broth with an organic solvent. In this situation, the recovery of cephalosporin C from the fermentation broth has hitherto usually been made by treating the fermentation broth with a large amount of an adsorber such as activated carbon, an anion-exchange resin, a cation-exchange resin or alumina so that the cephalosporin C is adsorbed by said adsorbent. The cephalosporin C which has been adsorbed by said adsorbent is then eluted out by means of a large volume of aqueous acetone or aqueous methanol. This adsorption-elution method of the prior art is disadvantageous in that it principally requires a vary large amount of the adsorbent and/or a very large volume of the aqueous organic solvent, and besides it can give only a low yield of cephalosporin C which amounts to about 40 – 50% at best, based on the initial cephalosporin C in the fermentation broth.

It has also been proposed to treat cephalosporin C present in the fermentation broth with 2,4,6-trinitrobenzenesulfonic acid, a lower alkoxycarbonyl chloride, an aralkoxycarbonyl chloride, isobornyloxycarbonyl chloride, a cycloaliphatic alkoxycarbonyl chloride, benzoyl chloride, an arylisocyanate or arylisothiocyanate, so that there is formed such a urethane derivative of cephalosporine C which is soluble in an organic solvent, and then to extract said urethane derivative out of the fermentation broth by means of an organic solvent (see, for example, German "Offenlegungschrift" Nos. 1933187 and 2262262; Japanese patent application prepublication Nos. 16692/72, 20189/72, 10077/73 and 68595/73). However, the urethane derivatives prepared in the letter prior art methods are not of a high solubility in an organic solvent and only enable the recovery efficiency of cephalosporin C to reach about 60% at most, as determined on the basis of the initial cephalosporin C content in the fermentation broth. Accordingly, it has long been sought for to provide such a process of recovering cephalosporin C from the fermentation broth or its filtrate and generally from an aqueous solution of cephalosporin C which may commercially be worked out in an economic and facile way and give a satisfactorily more improved recovery yield of cephalosporin C.

Therefore, an general object of this invention is to provide a novel means by which a more efficient recovery of cephalosporin C from the fermentation broth and generally from an aqueous solution of cephalosporin C can be made possible. A particular object of this invention is to provide new and useful cephem compounds which are derived from cephalosporin C and which are efficiently extractable from their aqueous solution with an organic solvent or are adsorbable by an ion-exchange resin or gel cellulose and readily elutable therefrom chromatographically. Another object of this invention is to provide such cephem compounds which are derived from cephalosporin C and are useful as intermediates easily convertible into further cephem derivatives, including ones having therapeutically useful antibacterial activity. Further object of this invention is to provide processes for the preparation of the cephem compounds of the above-mentioned types.

Still another objects of this invention will be clear from the following descriptions.

As a result of our extensive investigation, we have now found that new and useful cephalosporin C derivatives are produced by reacting a substituted alkoxycarbonyl chloride (which may also be termed as a chloroformate compound) with cephalosporin C in the aqueous fermentation broth filtrate and generally in an aqueous solution containing cephalosporin C, and that the new cephalosporin C derivatives, that is, the substituted alkoxycarbonylcephalosporin C so produced are efficiently and readily extractable from its aqueous solution with an organic solvent and also are adsorbable by an anion-exchange resin or gel cellulose and elutable from these adsorbers. On the basis of these findings, we have completed our invention.

Thus, we have now succeeded in preparing a new cephem derivative of the formula

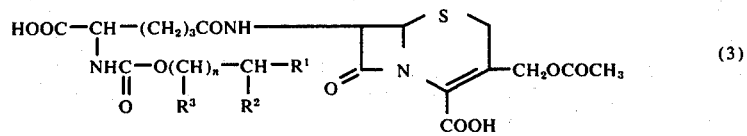 (3)

wherein $R^1$ is an aryloxy group such as phenoxy; an aralkyloxy group such as phenyl-lower alkyl group containing the alkyl of 1–4 carbon atoms, for example, benzyl; a lower alkoxy group such as methoxy, ethoxy, propoxy, isopropoxy, n-butoxy, sec-butoxy and isobutoxy; a lower alkoxy-alkoxy group and particularly of 2–7 carbon atoms such as methoxy-methoxy, methoxy-ethoxy, methoxy-butoxy, ethoxy-ethoxy, butoxy-ethoxy; or a halogen atoms such as chlorine, bromine, fluorine and iodine; $R^2$ and $R^3$ each is a hydrogen atom, methyl group, a halogen atom such as chlorine, bromine, iodine and fluorine; or a halomethyl group such as chloromethyl, bromomethyl, iodomethyl and fluoromethyl, and $n$ is an integer of 1 or 2, by admixing a chloroformate compound of the formula

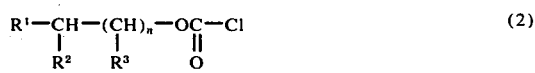 (2)

wherein $R^1$, $R^2$, $R^3$ and $n$ each has the same meaning as stated above with an aqueous solution and particularly the fermentation broth filtrate containing cephalosporin C of the formula

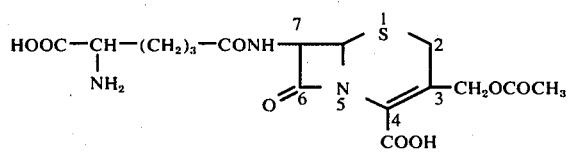 (1)

and thereby reacting said chloroformate compound with cephalosporin C in said aqueous solution, and subsequently recovering the reacted product of the formula (3) from the aqueous solution through an extraction using an organic solvent such as esters, ketones and alcohols and especially methylisobutylketone and n-butanol. The substituted alkoxycarbonylcephalosporin C of the formula (3) has its amino group blocked by means of the acyl radical

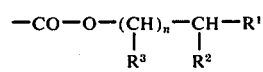

and hence shows an enhanced lipophilic property as compared to cephalosporin C itself, so that the cephem derivative of the formula (3) gains a high solubility in an organic solvent and is thus efficiently extractable from its aqueous solution by means of such an organic solvent in which the cephem derivative of the formula (3) is soluble but which is immiscible with water. In addition, it has now been found that the cephem derivative of the formula (3) can readily be adsorbed out of its aqueous solution by means of an anion-exchange resin or gel cellulose and hence can be isolated from the aqueous solution also by resorting to the adsorption procedure. Accordingly, it will be clear that the isolation and purification of the cephem derivative of the formula (3) may be achieved in an efficient and facile way, and that the cephem derivative of the formula (3)

is very valuable in providing a new means by which an efficient and facile recovery of cephalosporin C from its aqueous solution can be made possible in such a manner that cephalosporin C in its aqueous solution is once converted into the cephem derivative of the formula (3) and subsequently the cephalosporin C in the form of its cephem derivative of the formula (3) is isolated from the aqueous solution through the extraction procedure or the adsorption procedure.

Furthermore, the cephem derivative of the formula (3) is important and very valuable also from a viewpoint of chemical synthesis in that it provides a starting material from which there can readily be produced a variety of another useful cephem compounds, including 7-acylamidocephalosporanic acid, through further chemical conversion or modifications. Accordingly, this invention further include a conversion of the cephem derivative of the formula (3) into another useful cephem compounds of different kinds. In this connection, we have made further study to provide a new method for the conversion of the cephem derivative of the formula (3) into another useful cephem compounds which is operated in an efficient and facile way in a commercial scale.

A method for the preparation of the cephem derivative of the formula (3) is now described in detail.

A solution containing cephalosporin C of the above-mentioned structural formula (1) is at first admixed and reacted with at least an equi-molar proportion of a chloroformate compound of the formula (2)

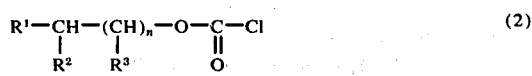 (2)

wherein $R^1$ represents an aryloxy group, an aralkyloxy group, a lower alkoxy group containing from 1 to 4 carbon atoms, a lower alkoxy-alkoxy group containing from 2 to 7 carbon atoms or a halogen atom, $R^2$ and $R^3$ are independently a hydrogen atom, a methyl group, a halomethyl group or a halogen atom, and $n$ is an integer of 1 to 2, to produce a cephem derivative of the general formula (3)

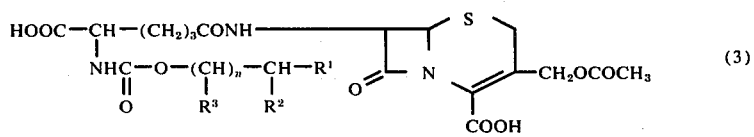 (3)

wherein $R^1$, $R^2$, $R^3$ and $n$ have the same meanings as defined above, respectively.

Examples of the chloroformate compound of the formula (2) (i.e., the substituted alkoxycarbonyl chloride) include: 2-methoxyethoxycarbonyl chloride, 2-ethoxyethoxycarbonyl chloride, 2-propoxyethoxycarbonyl chloride, 2-isopropoxyethoxycarbonyl chloride, 2-n-butoxyethoxycarbonyl chloride, 2-isobutoxyethoxycarbonyl chloride, 2-sec-butoxyethoxycarbonyl chloride, 2-tert-butoxyethoxycarbonyl chloride, 2-methoxypropoxycarbonyl chloride, 2-ethoxypropoxycarbonyl chloride, 2-propoxypropoxycarbonyl chloride, 2-isopropoxypropoxycarbonyl chloride, 2-n-butoxypropoxycarbonyl chloride, 2-isobutoxypropoxycarbonyl chloride, 2-sec-butoxypropoxycarbonyl chloride, 2-tert-butoxypropoxycarbonyl chloride, 2-phenoxyethoxycarbonyl chloride, 2-benzyloxyethoxycarbonyl chloride, 2-(2-methoxyethoxy)ethoxycarbonyl chloride, 2-(2-ethoxyethoxy)ethoxycarbonyl chloride, 2-(2-propoxyethoxy) ethoxycarbonyl chloride, 2-(2-butoxyethoxy)ethoxycarbonyl chloride, 2-(2-ethoxyethoxy)-propoxycarbonyl chloride, 2-(2-ethoxypropoxy)ethoxycarbonyl chloride, 2-chloroethoxycarbonyl chloride, 3-chloropropoxycarbonyl chloride, 1-chloromethyl-2-chloroethoxycarbonyl chloride, 2,3-dichloropropoxycarbonyl chloride, 2-bromoethoxycarbonyl chloride, 2-iodoethoxycarbonyl chloride, 2,2,2-trifluoroethoxycarbonyl chloride, 1-methyl-2-chloro-isopropoxycarbonyl chloride, 1-iodomethyl-α-iodoethoxycarbonyl chloride, 2,3-dibromopropoxycarbonyl chloride, 1-methyl-2-fluoroethoxycarbonyl chloride and 1-bromomethyl-2-bromoethoxycarbonyl chloride. It has been found that the compound of the formula (3) can be produced at a high yield, and can be extracted from the aqueous reaction solution at a high extraction yield and efficiency i.e., at an extraction yield of at least 72% using as the extracting organic solvent acetic esters such as ethyl acetate, ketones such as methylethyl ketone and alkanols of 3 or more carbon atoms such as n-butanol. Moreover, the compound of the formula (3) can easily and efficiently be separated from its solution in water or in an organic solvent by means of an adsorbent such as active carbon or an ion-exchange resin or a gel cellulose. Ion-exchange resins suitable for this purpose may be an anion-exchange resin such as Amberlite IRA-68 (a product sold by Rohm & Haas Co., U.S.A.), Amberlite IRA-401 (a product sold by Rohm & Haas Co., U.S.A.) and BIO-REX-5 (a product sold by Bio-Rad Laboratories, U.S.A.). Suitable adsorber may be DEAE-Sephadex (a product of Pharmacia Co., Sweden) and DEAE-cellulose (a product of Pharmacia Co., Sweden). The compound of the formula (3) which has been adsorbed by such an anion-exchange resin may be isolated therefrom by eluting with a buffered solution of sodium chloride and hydrochloric acid in water at pH 3.0. The compound of the formula (3) which has been adsorbed by DEAE-Sephadex or DEAE-cellulose may be isolated therefrom by eluting with an aqueous sodium chloride solution.

The above procedure or process making the cephem derivative of the formula (3) may be carried out as follows: A fermentation broth which has been obtained by culturing a cephalosporin C-producing strain such as Cephalosporium acremonium (see Japanese Patent Publication No. 190/1960) is filtered and the broth filtrate obtained is admixed with acetone, acetonitrile or tetrahydrofuran. Then, a solution of the substituted alkoxycarbonyl chloride of formula (2) in dry acetone, acetonitrile or tetrahydrofuran is added to the broth filtrate under agitation. The mixture may preferably be stirred at a reaction temperature of 0° to 30° C and for a reaction time of 1 to 5 hours. The reaction is continued under agitation while adding an alkaline solution (for example, aqueous sodium hydroxide or aqueous sodium phosphate solution) for maintaining the pH value of the reaction solution at 8.0 to 8.5. The reaction mixture is agitated for further 1 hour at a temperature of 0° to 30° C at a pH value of 8.0 to 8.5. Thereafter, a mineral acid or an organic sulfonic acid such as p-toluenesulfonic acid is added to the reaction solution to adjust the pH value to 4.0 to 7.0 and the acetone is removed by distillation under reduced pressure. Then, a suitable non-acidic inorganic salt such as sodium chloride is introduced into the resultant concentrate while maintaining the pH value at 2.0 by addition of a mineral acid (such as phosphoric acid), an organic acid (such as citric acid) or an organic sulfonic acid (such as benzenesulfonic acid, p-toluenesulfonic acid, or naphthalenesulfonic acid), followed by extracting the reaction product from the concentrated solution by means of an organic solvent which is immiscible with water but in which the compound of the formula (3) is soluble. Suitable examples of the extracting organic solvent available for this purpose includes esters, ketones and alcohols, but methyl ethyl ketone, methyl isobutyl ketone, methyl isopropyl ketone, acetic esters and n-butanol are preferred.

The organic solvent extract so obtained into which the compound of the formula (3) has been transferred from the fermentation broth filtrate is separated from the aqueous phase of the broth and is then extracted with a phosphate buffer solution at pH of 7, so that the compound of the formula (3) is again transferred into the phosphate buffer solution. This phosphate buffer solution containing the desired compound is then washed with ethyl acetate to remove the impurities, and the remaining aqueous phosphate solution containing the desired compound is adjusted to pH of 2 and further saturated with a suitable non-acidic inorganic salt such as sodium chloride and extracted with ethyl acetate several times to give the ethyl acetate extracts. The above procedure of extracting the phosphate buffer solution with ethyl acetate and of saturating said buffer solution with the salting-out agent is again repeated. The resulting ethyl acetate extracts containing the desired compound of the formula (3) are combined together, washed with a saturated solution of the non-acidic inorganic salt such as NaCl in water, dried over anhydrous magnesium sulfate and then distilled in vacuo to remove the ethyl acetate. The resulting concentrated solution is admixed with petroleum ether to precipitate the desired compound of the formula (3). Instead of the above-mentioned extraction procedure using an organic solvent, it is also possible to employ such an adsorption procedure as stated hereinbefore, for the purpose of recovering the compound of the formula (3) from the fermentation broth filtrate or generally from an aqueous solution containing the compound of the formula (3).

According to an aspect of the present invention, therefore, there is provided as a new and useful compound a cephem derivative of the formula (3)

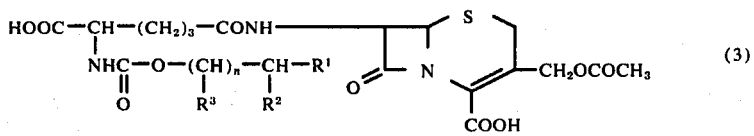

(3)

wherein $R^1$ is an aryloxy group, an aralkyloxy group, a lower alkoxy group, a lower alkoxy-alkoxy group or a halogen atom; $R^2$ and $R^3$ each is a hydrogen atom, methyl group, a halogen atom or a halomethyl group; and $n$ is an integer of 1 to 2.

According to the other aspect of the present invention, there is provided a method for the preparation of the cephem derivative of the above formula (3), which comprises admixing a chloroformate compound of the formula (2)

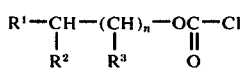

(2)

wherein $R^1$, $R^2$, $R^3$ and $n$ each has the same meaning as defined in the above formula (3), with a solution containing cephalosporin C, and thereby reacting said chloroformate compound with cephalosporin C in said solution to produce the cephem derivative of the above formula (3).

According to a further aspect of the present invention, there is provided a process of recovering cephalosporin C from its aqueous solution in an improved yield, which comprises admixing a chloroformate compound of the formula (2)

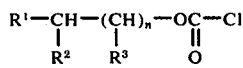

(2)

wherein $R^1$ is an aryloxy group, an aralkyloxy group, a lower alkoxy group, a lower alkoxy-alkoxy group or a halogen atom; $R^2$ and $R^3$ each is a hydrogen atom, methyl group, a halogen atom or a halomethyl group; and $n$ is an integer of 1 to 2, with an aqueous solution containing cephalosporin C and thereby reacting said chloroformate compound with cephalosporin C in said aqueous solution to produce a cephem derivative of the formula (3)

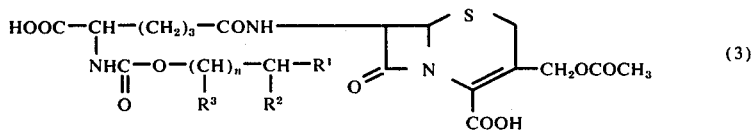

(3)

wherein $R^1$, $R^2$, $R^3$ and $n$ each has the same meaning as defined above, and then recovering the cephalosporin C in the form of its cephem derivative of the above formula (3) from said aqueous solution either by extracting with an organic solvent in which said cephem derivative is soluble but which is immiscible with water, or by adsorbing by means of a solid adsorbent by which said cephem derivative is adsorbable. According to a preferred embodiment of this process of the present invention, cephalosporin C may be recovered from its aqueous solution in an excellent yield of at least 90% based on the initial content of cephalosporin C in its aqueous solution, including the fermentation broth or its filtrate, by reacting a chloroformate compound of the formula (2')

(2')

wherein $R_a^1$ is a halogen atom and particularly chlorine and bromine, or a lower alkoxy group of 1–4 carbon atoms and particularly butoxy group or phenoxy group, with cephalosporin C and then recovering the resulting cephem derivative from the solution by extracting with an organic solvent chosen among ethyl acetate, methyl ethyl ketone, methyl isopropyl ketone, methyl isobutyl ketone and n-butanol or by adsorbing an anion-exchange resin containing amino groups as the anion-exchange functions thereof such as Amberlite IRA-68.

The cephem derivative of the formula (3) prepared in the above process may further be converted into another cephem derivative by reacting with a neucleophilic reagent to attack the acetoxymethyl group at the 3-position of the cephem ring of the compound. Thus, when the cephem derivative of the formula (3) is reacted with a nucleophilic reagent of the formula (4)

$R^4H$ (4)

wherein $R^4$ is azido group —$N_3$ or a nucleophilic residue of the formula —SY in which Y is a heterocyclic group such as thiadiazolyl, triazoyl, tetrazolyl, oxadiazolyl, pyridine-N-oxide-yl, pyrimidinyl, pyridazinyl, isoxazolyl, pyrazolyl, etc. in a solution in a suitable organic solvent such as acetone, ethyl ether and the like, there is produced a cephem derivative of the formula (5)

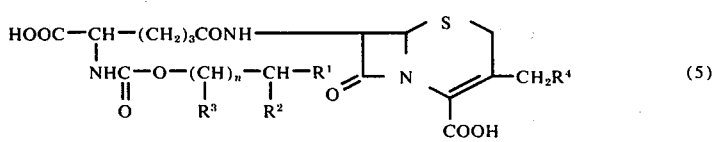

(5)

wherein $R^1$, $R^2$, $R^3$, $R^4$ and $n$ each has the same meaning as defined above. This cephem derivative of the formula (5) is useful as intermediate to produce another cephem compounds through further chemical modifications.

The reaction of the cephem derivative of the formula (3) with the nucleophilic reagent of the formula (4) may be carried out as follows: The cephem derivative of the formula (3) and the nucleophilic reagent of the formula (4) are dissolved in equimolar or substantially equimolar proportions in a suitable organic solvent inert to the reactants, such as acetone, ethyl ether, chloroform, methanol, ethanol, dimethylsulfoxide, dimethylformamide and nitrobenzene or in water, and the mixture is heated at a reaction temperature preferably of 40° – 65° C for a reaction time of 6 – 50 hours under stirring to effect the reaction. This reaction may preferably be performed while the pH in the reaction mixture is maintained in a range of 5.0 – 8.0 by occasional addition of aqueous alkali or mineral acid. The cephem reactant of the formula (3) may also be employed in the form of its mono- or dicarboxylate with a lower alkanol. The nucleophilic reagent of the formula (4) may be an alkali metal azide or an alkaline earth metal azide or a heterocyclic compound containing a mercapto group —SH represented by the formula Y—SH where Y has the same meaning as stated above or its alkali mercaptide derivative of the formula Y—SM' where M' stands for an alkali metal such as sodium.

Examples of the nucleophilic reagent of the formula (4) include sodium azide, mercapto-1,3,4-oxadiazole, mercapto-1,2,4-oxadiazole, mercapto-1,2,5-oxadiazole, mercapto-1,2,4-thiadiazole, mercapto-1,3,4-thiadiazole, mercapto-1,2,5-thiadiazole, mercapto-thiazole, mercapto-tetrazole, mercapto-pyridine-N-oxide, mercapto-pyridazine, mercapto-isoxazole, mercapto-pyrazole, mercapto-pyrimidine-N-oxide, mercapto-pyrimidine, mercapto-isothiazole, mercapto-pyrazinine, mercapto-3-methoxypyridazine-N-oxide and mercapto-imidazole-N-oxide. These heterocyclic compounds may have a substituent such as a lower alkyl group or alkoxy group such as methyl, ethyl, propyl, isopropyl, isobutyl, methoxy or ethoxy group on the heterocyclic ring.

The reaction of the cephem derivative of the formula (3) with the nucleophilic reagent of the formula (4) may be illustrated in the following particular reaction. N-(2-chloroethoxycarbonyl) cephalosporin C and 2-mercapto-5-methyl-1,3,4-thiadiazole are added to water, and the mixture is heated at a temperature of 60° to 65° C for 6.5 hours while maintaining the pH value at 5.5 to 6.5 by addition of sodium hydrogen carbonate. Then, acetone is added to the reaction solution to deposit an oily material, which is the separated from the reaction solution. The oily material so separated is then triturated together with an amount of acetone added thereto, giving a solid material which is identified as a di-sodium salt of 7-[5-(2-chloroethoxycarbamido)adipinamido]-3-(5-methyl-1,3,4-thiadiazole-2-ylthiomethyl)-3-cephem-4-carboxylic acid at a yield of 83% or more.

The cephem derivative of the formula (3) as well as the cephem derivative of the formula (5) are new and useful compound as will be clear from the foregoing descriptions. Both the cephem derivatives of the formulae (3) and (5) may generically be represented by a cephem compound of the following general formula (3').

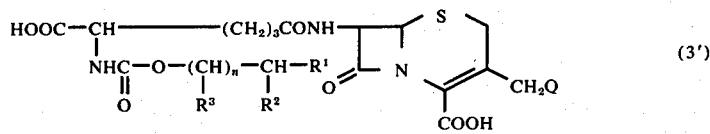
(3')

wherein $R^1$ is an aryloxy group, an aralkyloxy group, a lower alkoxy group, a lower alkoxy-alkoxy group or a halogen atom; $R^2$ and $R^3$ each are independently a hydrogen atom, methyl group, a halomethyl group or a halogen atom; Q is acetoxy group, azido group —$N_3$ or a nucleophilic residue; and $n$ is an integer of 1 to 2.

The cephem derivative of the above formula (3) may further be converted into a 7-acylamidocephalosporanic acid and 7-amino-cephalosporanic acid which is known as a useful intermediate for use in chemical synthesis of many therapeutically active cephem compounds, in such a manner that the cephem derivative of the formula (3) is treated successively with a known carboxyl-protecting agent, with an iminohalogenating agent, with an alcohol, with an acylating agent and finally with a hydrolyzing agent. It will be evident that the cephem derivative of the formula (5) may be converted in a similar way into the corresponding 3-substituted 7-acylamidocephalosporanic acid or 3-substituted 7-aminocephalosporanic acid in which the 3-substituent in the cephem ring thereof is the group —$CH_2R^4$ where $R^4$ is as defined above.

The conversion of the cephem derivative of the formula (3) into a 7-acylamidocephalosporanic acid is now described schematically by the following formula:

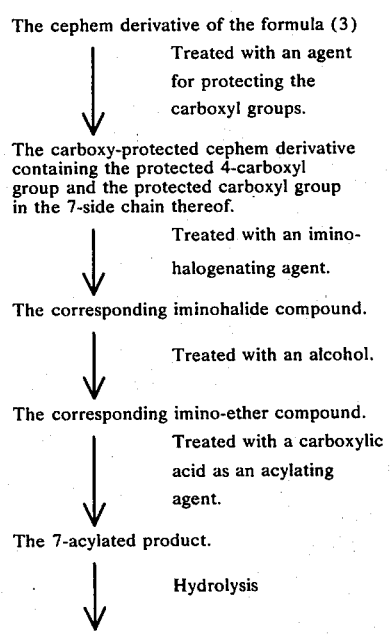

-continued
7-Acylamidocephalosporanic acid.

The protecting agent for carboxyl group available in the above reaction scheme may be classified into the following two groups:
1. A compound having the following formula (6)

(6)

(wherein M is a silicon atom or a carbon atom; $R^5$, $R^6$ and $R^7$ may be same or the different and are a halogen atom; a lower alkyl group which may be substituted by a substituent; a lower alkoxy group which may be substituted by a substituent; or an oxygen atom; and X is a halogen atom); and 2. A compound having a formula (7)

(7)

[wherein $R_a^5$ and $R_a^6$ may be same or the different and are a halogen atom or a lower alkoxy group (or $R_a^5$ and $R_a^6$ taken together may form an alkylenedioxy group —O—$(CH_2)_m$—O— where m is 1, 2, 3 or 4), P is phosphorus, and X is a halogen atom].

Examples of the compounds of the formula (6) include $SiCl_4$, $CH_3OS;Cl_3$, $C_2H_5OSiCl_3$, $(CH_3O)_2SiCl_2$, $(C_2H_5O)_2SiCl_2$, $(CH_3)_3SiCl$, $(CH_3)_2SiCl_2$, $(C_2H_5)_3SiCl$, $(CH_3O)_2SiCl$, $CH_3SiCl_3$ and $CH_3(CH_3O)SiCl_2$, $(CH_3O)_3SiCl$, $COCl_2$, $CH_3COCl$, $CH_3OCOCl$, $C_2H_5OCOCl$, $(CH_3)_2(CH_3O)SiCl$.

The compound of the formula (3) is reacted with the compound of the formula (6) so that the two carboxyl groups present in the compound of the formula (3) are protected by the group

The resultant carboxyl-protected derivative is then interacted with the iminohalogenating agent in an anhydrous organic solvent in the presence of an acid-binding agent. The acid-binding agent is, for example, a tertiary amine such as a trialkylamine, pyridine and its homologs, quinoline and its homologs, N, N-dialkylarylamine, N-alkylmorpholine, N-alkylpiperidine or the like. Particularly, N, N-dimethylaniline, N, N-diethylaniline, N, N-dimethyltoluidine, quinoline and pyridine are preferred.

Furthermore, examples of the anhydrous organic solvent include methylene chloride, chloroform, ethylene chloride, trichloroethylene, carbon tetrachloride, trichloroethane, tetrahydrofuran, dioxane, ethylene glycol dimethyl ether, acetone, benzene, toluene, xylene, ethyl acetate and the like. Among them, methylene chloride, chloroform and ethylene chloride are preferable.

Iminohalogenating agent is, for example, phosphorous pentachloride, phosphorous pentabromide, phosphorous trichloride, phosphorous tribromide, thionyl chloride, phosgene, phosphorous oxychloride, protocatechuonylphosphorous chloride, toluenesulfonyl chloride or the like. Among them, phosgene, and phosphorous pentachloride are preferable.

The iminohalide compound which has been derived from the reaction of the compound of formula (3) with the iminohalogenating agent is then reacted with an alcohol of the formula (8)

$R^8OH$ (8)

(wherein $R^8$ is either a lower alkyl group which may be substituted by a substituent such as a halogen atom or a hydroxy group or a lower alkoxy group; or an aralkyl group which may be substituted by a substituent such as a halogen atom or a lower alkyl group). Examples of the alcohol of the formula (8) may be an alkanol such as methyl alcohol, ethyl alcohol, n-propyl alcohol, iso-propyl alcohol, n-butyl alcohol, isobutyl alcohol, amyl alcohol, 2-ethylhexyl alcohol; benzyl alcohol, ethylene chlorohydrin, ethylene glycol monomethyl ether, ethylene glycol monoethyl ether, cyclohexanol, propyleneglycol, butyleneglycol and the like.

The reaction velocity varies depending upon the kind of the alcohol employed, i.e., the use of a lower alkanol accelerates the reaction velocity but that of a higher alkanol makes the velocity slower. Accordingly, the reaction temperature and time should suitably be chosen depending upon the kind of the alcohol. For instance, when using methanol, the reaction completes at −10° C in about 2 hours. The resultant reaction product is then treated in the presence of an acid-binding agent as mentioned hereinbefore with a reactive agent derived from a carboxylic acid represented by a formula (9).

(9)

wherein $R^9$ is a hydrogen atom, a cyano group; an alkyl group, an aryl group, an aralkyl group, an alkoxy group, an aryloxy group, a cycloalkyl group, a cycloalkenyl group or a heterocyclic group, which may be substituted by a substituent, respectively; and $R^{10}$ is a hydrogen atom, a halogen atom, a hydroxyl group, an amino group, an alkylamino group, a substituted amino group expressed by —$NHR^{11}$ (in which $R^{11}$ is a tertiary alkoxycarbonyl group such as t-butoxycarbonyl group, t-amyloxycarbonyl group, o-nitrobenzyloxycarbonyl group, p-nitrobenzyloxycarbonyl group or 2,2,2-trichloroethoxycarbonyl group; an aralkyloxycarbonyl group such as benzyloxycarbonyl group, or an enamine group), azido group, an alkylthio group, an alkoxycarbonyl group or a carb moyloxy group. Examples of the carboxylic acid of the formula (9) include α-chlorophenylacetic acid, α-bromophenylacetic acid, α-azidophenylacetic acid, α-acetoxyphenylacetic acid, α-propionyloxyphenylacetic acid, α-benzoyloxythienylacetic acid, α-t-butyryloxy-(p-methoxyphenyl)acetic acid, α-valeryloxy-(p-nitrophenyl)acetic acid, α-t-amyloxycarbonyloxyphenylacetic acid, α-t-butyloxycarbonyloxyphenylacetic acid, α-(2,2,2-trichloroacetoxy)phenylacetic acid, α-(β-halogenoethoxycarbonyloxy)thienylacetic acid, α-(phenylacetoxy)phenylacetic acid, α-benzyloxycarbonyloxyphenylacetic acid, α-(p-nitrobenzyloxy)thienylacetic acid, α-(p-halogenophenoxyacetoxy)phenylacetic acid, α-N-(2,2,2-trichloroethoxycarbonyl)aminophenylacetic acid, α-N-(benzyloxycarbonyl)aminophenylacetic acid, α-N-(t-butoxycarbonyl)aminophenylacetic acid, α-N-(1-carbamoylpropene-2-yl)aminophenylacetic acid, α-N-(t-amyloxycarbonyl)aminophenylacetic acid, α-N-(o-nitrobenzyloxycarbonyl)aminophenylacetic acid, α-N-(p-nitrobenzyloxycarbonyl)aminophenylacetic acid, aminophenylacetic acid, α-carbamoyloxyphenylacetic acid, mandelic acid, α-methylthiophenylacetic acid, α-ethoxycarbonyloxyphenylacetic acid, α-carbamoyloxyphenylacetic acid, thienylacetic acid, pyridylmercaptoacetic acid, tetrazolylacetic acid, 1-aminocyclohexanecarboxylic acid, α-aminocyclohexadienylacetic acid, α-aminocyclohexenylacetic acid, cyanoacetic acid and the like.

Furthermore, the reactive derivative of the carboxylic acid may, for example, be an acid halide, an acid anhydride, a mixed acid anhydride, an active ester, an acid azide, an acid cyanide or an active acid amine of the acid. Among them, the acid halide is preferable.

The resultant acylated product is, after isolation thereof or in situ in the reaction mixture, subjected to hydrolysis under acidic conditions, i.e., at a pH value of about 2, to liberate the unrequired part of the side chain at the 7-position of the cephem ring and to remove the carboxyl-protecting group, affording a 7-acylamidocephalosporanic acid of a formula (10)

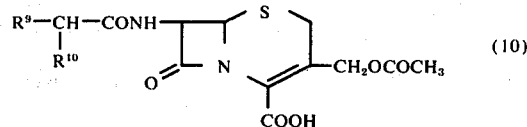

(wherein $R^9$ and $R^{10}$ each is as defined hereinbefore).

Typical examples of the product of the formula (10) are listed below:
- 7-(2-thienylacetamido)cephalosporanic acid,
- 7-(α-4-pyridylthioacetamido)cephalosporanic acid,
- 7-cyanoacetamidocephalosporanic acid,
- 7-(α-aminophenylacetamido)cephalosporanic acid,
- 7-(1-1H-4-tetrazolylacetamido)cephalosporanic acid,
- 7-(α-carbamoyloxyphenylacetamido)cephalosporanic acid,
- 7-(α-trichloroethoxycarbonyloxyacetamido)cephalosporanic acid,
- 7-(α-t-butyryloxy-p-methoxyphenylacetamido)cephalosporanic acid,
- 7-(α-t-amyloxycarbonyloxyphenylacetamido)cephalosporanic acid,
- 7-(α-p-nitrobenzyloxythienylacetamido)cephalosporanic acid,
- 7-(α-N-t-amyloxycarbonylaminophenylacetamido)cephalosporanic acid,
- 7-(α-N-2,2,2-trichloroethoxycarbonylaminophenylacetamido)cephalosporanic acid and the like.

Although the preparation of the 7-acylamidocephalosporanic acid of the formula (10) has been described above with regard to the use of the compound of formula (6) as the carboxyl-protecting agent, it will be self-evident that the same product of the formula (10) can be obtained in the same manner as described above also when the phosphorus compound of the formula (7) is used as the carboxyl-protecting agent.

The phosphorus compound of formula (7) may, for example, be $PCl_3$, $PBr_3$, $CH_3OPCl_2$, $(CH_3O)_2PCl$, $C_2H_5OPCl_2$, $C_3H_7OPCl_2$, $C_4H_9OPCl_2$, $(C_2H_5O)_2PCl$, $(C_3H_7O)_2PCl$, $(C_4H_9O)_2PCl$,

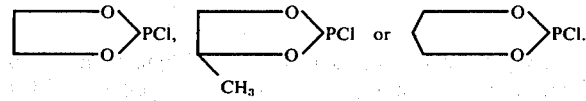

Moreover, the imino-ether compound which is derived from the treatments of the cephem derivative of the formula (3) with the carboxyl-protecting agent (6) or (7), with the iminohalogenating agent and with the alcohol of formula (8) may directly be hydrolyzed before treating with the reactive derivative of the aforementioned carboxylic acid of the formula (9). This direct hydrolysis gives 7-aminocephalosporanic acid of the formula (11):

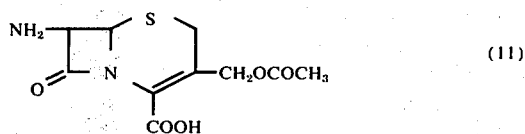

When the above-mentioned imino-ether compound is directly hydrolyzed into the 7-aminocephalosporanic acid of the formula (11), there may successfully be employed, irrespective of the nature of the carboxyl-protecting agent (6) or (7) used, the following hydrolyzing procedure: A solution (or the reaction solution) containing said imino-ether compound in an organic solvent together with an organic acid salt is poured into water or a mixture of water and a lower alkanol such as methanol, and the admixture is agitated at a temperature of 0° C to ambient temperature at an acidic pH of about 2 for a time sufficient to effect the hydrolysis. When the pH of the reaction is then adjusted by addition of an aqueous alkali to a pH of the iso-electric point for the desired compound 7-aminocephalosporanic acid, there is deposited the desired hydrolysis acid product. Said organic acid salt may suitably be selected from sodium formate, ammonium formate, sodium tartrate, sodium citrate, sodium acetate and sodium monochloroacetate.

From the foregoing descriptions, it will be apparent that the cephem derivative of the formula (5) may also be converted into the corresponding 3-substituted 7-acylamidocephalosporanic acid derivative of the following formula (12)

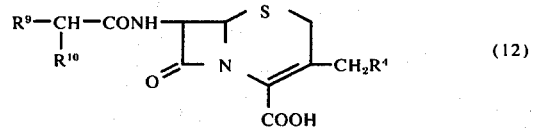

wherein $R^4$, $R^9$ and $R^{10}$ each is as defined above, or into the corresponding 3-substituted 7-aminocephalosporanic acid derivative of the formula (13)

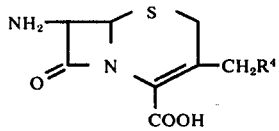

(13)

wherein R⁴ is as defined above, by treating in the same manner as the cephem derivative of the formula (3) is converted into the 7-acylamidocephalosporanic acid of the formula (10) or the 7-aminocephalosporanic acid of the formula (11) through the above-mentioned successive treatments.

The present invention is now illustrated with reference to the following Examples to which the present invention is not limited.

EXAMPLE 1

A fermentation broth containing cephalosporin C which had been obtained from the cultivation of a strain of *Cephalosporium acremonium* was adjusted to pH of 6 – 7 by addition of an aqueous hydrochloric acid and filtered to remove the cells.

The resulting broth filtrate contained cephalosporin C in an amount of 2000 γ/ml.

10 l of the filtrate was washed three times with 3 l portions of ethyl acetate for removal of a fat-soluble fraction therefrom. Then, 1 l of acetone was added to the aqueous broth filtrate, to which was further added a 20% sodium hydrogen phosphate solution to adjust the pH to 8 to 8.5. To the resultant solution (the filtrate) was dropwise added with agitation a solution which contained 26 g of 2-n-butoxyethoxycarbonyl chloride dissolved in 0.5 l of dry acetone, at a temperature of 15° – 25° C over about 2 hours, during which the pH value of the reaction solution was maintained at 8 – 8.5 by addition of a 20% sodium hydrogen phosphate. After completion of the addition, the solution was continuously agitated for further 1 hour at 15° – 25° C and at a pH of 8 to 8.5.

After the completion of the reaction, the reaction mixture (the reaction solution) was adjusted to pH of 6.5 – 7.0 and the acetone was distilled off from the solution at room temperature in vacuo. The solution so concentrated was admixed with 1 kg of sodium chloride and then with an aqueous solution of 10% phosphoric acid to adjust the pH to 2.0. The solution was subsequently extracted with 1.5 l, 1 l and 1 l portions of n-butanol to give the n-butanol extracts in which the N-(2-n-butoxyethoxycarbonyl) cephalosporin C product was dissolved.

The resulting n-butanol extracts were combined together and then extracted three times with 0.6 l aliquots of a 0.2 M phosphate buffer solution at pH of 6.5 to transfer the cephalosporin C derivative into the phosphate buffer solution, which was then washed with 0.5 l of ethyl acetate. The remaining aqueous phase (the aqueous phosphate buffer solution portion) was adjusted to an acidic pH of 2.0 by addition of 10% aqueous phosphoric acid, saturated with sodium chloride added thereto and then extracted three times with 0.5 l, 0.3 l and 0.3 l portions of ethyl acetate. The ethyl acetate extracts so obtained were combined together and then washed with 0.5 l of a saturated aqueous solution of sodium chloride and dried over anhydrous magnesium sulfate. The ethyl acetate extract so dried was then distilled in vacuo to remove the ethyl acetate solvent, and the concentrated solution was admixed with petroleum ether, affording 37.2 g of a crude product of N-(2-n-butoxyethoxycarbonyl) cephalosporin C (66% purity). The recovery yield of the cephalosporin C component amounted to 91.2% as measured on the basis of the initial content of cephalosporin C present in the fermentation broth filtrate.

10 g of the crude cephalosporin C derivative (66% purity) was dissolved in 100 ml of water, and the solution was then saturated with sodium chloride and adjusted to pH 2.0 by adding 10% phosphoric acid. The resultant solution was extracted three times with 50 ml aliquots ethyl acetate. The ethyl acetate extracts were combined together and in turn extracted three times with 40 ml portions of a 0.2 M aqueous phosphate buffer solution (at a pH of 6.5).

The resultant extract in the phosphate buffer solution was saturated with sodium chloride, adjusted to pH of 2.0 by addition of 10% aqueous phosphoric acid and then extracted three times with 50 ml aliquots of ethyl acetate. The resultant ethyl acetate solution was washed with 50 ml of a sodium chloride saturated solution, followed by drying over anhydrous magnesium sulfate and removing the solvent under a reduced pressure. The resultant concentrate was added with a mixture of ether and petroleum ether to precipitate 6.4 g of N-(2-n-butoxyethoxycarbonyl) cephalosporin C monohydrate (91% purity).

A silica gel thin-layer chromatogram (using a developing solvent of 1:2 acetone-methanol showed a spot of N-(2-n-butoxyethoxycarbonyl) cephalosporin C at $R_f$ of 0.56.

This cephalosporin C derivative could further be purified by a silica gel chromatography (using a mixture of 9:1 chloroform-methanol as a developing solvent).

Furthermore, where the above-procedures for the extraction of the cephalosporin C derivative was repeated with magnesium sulfate instead of sodium chloride as the salting-out agent, the cephalosporin C could be recovered at a yield of 89.6%.

The cephalosporin C derivative had the following characteristic properties:

Melting Point: 76° to 79° C

Ultra-violet Absorption Spectrum: $\lambda_{max}^{methanol} = 263$ mμ and ε = 7500

Infra-red Absorption Spectrum (by a disk method using KBr): 1790 cm$^{-1}$

Element Analysis: Calculated for $C_{23}H_{33}N_3O_{11}S \cdot H_2O$: C, 47.82%, H, 6.10%, N, 7.27%. Found: C, 47.56%, H, 5.97%, N, 7.12%.

EXAMPLE 2

10 l of the broth filtrate which was obtained in the same manner as in Example 1 was washed three times with 1 l portions of ethyl acetate to remove the fat-soluble fraction therefrom. Then, 3 l of acetone was then added to the filtrate, to which was added a 1N sodium hydroxide solution to adjust the pH of the filtrate to 8 to 8.5. Thereafter, a solution of 13.6 g of 2-methoxyethoxycarbonyl chloride in 0.5 l of dry acetone was dropwise added with agitation to the resultant filtrate solution at 10° to 20° C over about 2 hours while maintaining the pH value at 8 to 8.5 by addition of a 1N sodium hydroxide solution. After completion of the addition, the filtrate solution was continuously agitated for further 1 hour at 10° C to 20° C at a pH value of 8 to 8.5 for reaction.

After completion of the reaction, the reaction solution was adjusted to pH of 6.5 to 7.0 and acetone was removed by distillation at room temperature under a reduced pressure, followed by addition of 1 kg of sodium chloride and a 10% phosphoric acid solution to adjust the pH to 2.0. Then, the resultant solution was extracted with 1.5 l, 1 l and 1 l portions of n-butanol to separate the desired reaction product.

Thereafter, the resultant n-butanol extract was in turn extracted three times with 0.6 l portion of 0.2 M phosphate buffer solution (at pH of 6.5). The phosphate buffer solution containing the desired reaction product was washed with 0.5 l of ethyl acetate. The separated aqueous phase was saturated with sodium chloride, followed by addition of a 10% phosphoric acid solution to adjust the pH to 2.0 and further extracted with 0.5 l, 0.3 l and 0.3 l portions of ethyl acetate. The resultant solutions (extracts) of the cephem compound in ethyl acetate were combined together and the solution was washed with a saturated aqueous sodium chloride solution and dried over anhydrous magnesium sulfate, followed by removing the solvent by distillation under a reduced pressure. The resultant residue was treated with petroleum ether to give 25.3 g of crude N-(2-methoxyethoxycarbonyl) cephalosporin C (65% purity). The recovery yield of the cephalosporin C was 73.2% based on the cephalosporin C content in the fermentation broth filtrate.

Then, 10 g of the crude cephalosporin C derivative (66% purity) was treated in the same manner as in Example 1 to afford 6.1 g of N-(2-methoxyethoxycarbonyl) cephalosporin C (96% purity).

In a silica gel thin-layer chromatogram (using a 1:2 mixture of acetone and methanol as the developing solvent), the N-(2-methoxyethoxycarbonyl) cephalosporin C occurred in a spot at $R_f$ of 0.50.

When the above procedure was repeated using potassium chloride as the salting-out agent, the recovery yield was 75.8% based on the cephalosporin C content in the fermentation broth filtrate.

This cephalosporin C derivative had the following characteristic portions:

Ultraviolet Absorption Spectrum: $\lambda_{max}^{methanol} = 262$ m$\mu$ and $\epsilon = 7450$ Infra-red Absorption Spectrum (determined by a disk method using KBr): 1790 cm

EXAMPLE 3

10 l of the broth filtrate which was obtained in the same manner as in Example 1 was washed three times with ethyl acetate. Then, the washed filtrate was added with 1 l of acetone and then with a 1N sodium hydroxide solution to adjust the pH to 8 to 8.5. A solution of 32 g of 2-(2-n-butoxyethoxy)ethoxycarbonyl chloride in 0.5 l of dry acetone was dropwise added into the resultant solution while agitating at 10° to 20° C over about 2 hours, during which the pH of the reaction solution was adjusted to 8 to 8.5 by addition of a 1N sodium hydroxide solution.

After completion of the addition of the chloride reactant, the reaction was further continued under agitation at a temperature of 10° to 20° C at a pH of 8 to 8.5 for 1 hour. After completion of the reaction, the reaction solution was adjusted to pH of 6.5 to 7.0 by addition a 10% phosphoric acid solution, followed by removal of acetone by distillation at room temperature under a reduced pressure and addition of 1 kg of sodium chloride and of a 10% phosphoric acid solution to adjust the pH to 2.0. Then, the thus treated reaction solution was extracted with 1.5 l, 1 l and 1 l portions of n-butanol.

The resultant n-butanol extracts were combined and the solution was in turn extracted three times with 0.6 l portions of a 0.2 M phosphate buffer solution (having a pH of 6.5). The phosphate buffer solution containing the desired cephem compound was washed with 0.5 l of ethyl acetate and saturated with sodium chloride, followed by three extraction with 0.5 l, 0.3 l and 0.3 l portions of ethyl acetate at pH 2.0. The resultant ethyl acetate solutions were combined together and the solution was washed with a saturated aqueous solution of sodium chloride and dried over anhydrous magnesium sulfate, followed by distillation for removing the solvent from the solution under reduced pressure. The resultant residue was added with petroleum ether to give 40.1 g of a crude N-[2-(2-n-butoxyethoxy)-ethoxycarbonyl] cephalosporin C (63% purity). The recovery yield was 82.0% based on the cephalosporin C content in the fermentation broth.

10 g of the crude cephalosporin C derivative (63% purity) was treated in the same manner as in Example 1 to afford 6.4 g of a pure

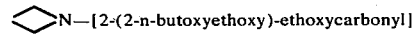

cephalosporin C dihydrate (88.5% purity).

In a silica gel thin-layer chromatogram (using a 1:2 mixture of acetone and methanol as a developing solvent), N-[2-(2-n-butoxyethoxy)ethoxycarbonyl] cephalosporin C was identified at a spot of $R_f$ of 0.67.

When the above process was repeated using sodium sulfate instead of sodium chloride as the salting-out agent, the recovery yield was 80.4% in terms of the cephalosporin C content of the fermentation broth filtrate.

The cephalosporin C derivative had the following characteristics:

Melting Point: 76° to 82° C (decomposed)

Ultraviolet Absorption Spectrum: $\lambda_{max}^{methanol} = 260$ and $\gamma = 7450$ Infra-red Absorption Spectrum (determined by a disk Method using KBr): 1790 cm$^{-1}$ Elementary Analysis: Calculated for $C_{25}H_{37}N_3O_{12}S \cdot 2H_2O$: C, 46.94%; H, 6.46%; N, 6.57%. Found: C, 46.79%; H, 6.27%; N, 6.61%.

EXAMPLE 4

10 l of the broth filtrate which was obtained in the same manner as in Example 1 was washed three times with 3 l portions of ethyl acetate. Then, the washed filtrate was added with 1 l of acetone and adjusted to pH of 8 to 8.5 by addition of a 20% aqueous sodium hydrogen phosphate solution. To the solution (filtrate) was dropwise added a solution of 26.5 g of 2-(2-methoxyethoxycarbonyl chloride in 0.5 l of dry acetone, while agitating at a temperature of 10° to 20° C over about 2 hours and while the pH of the reaction solution was maintained at 8 to 8.5 by occasional addition of a 20% sodium hydrogen phosphate solution. After completion of the addition of the chloride reagent, the reaction solution was continuously agitated for about 1 hour at a temperature of 10° to 20° C at the same pH value. After completion of the reaction, the reaction solution was adjusted to pH of 6.5 to 7.0 and the acetone was removed therefrom by distillation at room temperature under a reduced pressure, followed by addition of 1 kg of sodium chloride and adjustment of the pH to 2.0 by addition of a 10% phosphoric acid solution. The resultant reaction mixture was extracted with 1.5 l, 1 l and 1 l portions of n-butanol.

The thus obtained n-butanol extracts containing of the cephem product were combined together and again extracted three times with 0.6 l portions of a 0.2 M phosphate (at pH 6.5). Then, the remaining aqueous buffer solution was washed with 0.5 l of ethyl acetate which was, in turn, saturated with sodium chloride and added with a 10% phosphoric acid solution to adjust the pH to 2.0, followed by extraction with 0.5 l, 0.3 l and 0.3 l portions of ethyl acetate. The resultant ethyl acetate extracts containing the desired cephem compound was washed with a sodium chloride-saturated aqueous solution and dried over anhydrous magnesium sulfate, followed by distillation of the solvent under reduced pressure. To the resultant residue was added petroleum ether to give 32.5 g of a crude N-[2-(2-methoxyethoxy)-ethoxycarbonyl] cephalosporin C product (60% purity).

The recovery yield of the cephem derivative was 72.1% in terms of the cephalosporin C content in the starting fermentation broth filtrate.

10 g of the crude cephem product was treated in the same manner as in Example 1 to afford 6.1 g of N-[2-(2-methoxyethoxy)-ethoxycarbonyl] cephalosporin C dihydrate (90.5% purity).

A slica gel thin-layer chromatogram (using a 1:2 mixture of acetone and methanol) gave a spot of N-[2-(2-methoxyethoxy)-ethoxycarbonyl] cephalosporin C at $R_f$ of 0.60.

This cephalosporin C derivative had the following characteristic properties:
 Melting Point: 52° to 66° C
 Ultraviolet Absorption Spectrum: $\lambda_{max}^{methanol} = 260$ m$\mu$ and $\epsilon = 7500$
 Infra-red Absorption Spectrum (determined by a disk method using KBr): 1790 cm$^{-1}$
 Elementary Analysis: Calculated for $C_{22}H_{31}N_3O_{12}S \cdot 2H_2O$: C, 44.22%; H, 5.90%; N, 7.03%. Found: C, 44.48%; H, 5.92%; N, 6.81%.

EXAMPLE 5

10 l of the broth filtrate which was obtained in the same manner as in Example 1 was washed three times with 3 l portions of ethyl acetate, and then admixed with 1 l of acetone and the pH was maintained at 8 to 8.5 by addition of an 1N sodium hydroxide solution. To the resultant solution was further dropwise added with agitation a solution of 29 g of 2-phenoxyethoxycarbonyl chloride in 0.5 l of dry acetone, at a temperature of 10° to 20° C over about 2 hours while maintaining the pH at 8 to 8.5 by addition of a 1N sodium hydroxide solution.

After completion of the addition of the chloride reagent, the reaction mixture was continuously agitated for further 1 hour at the same temperature at the same pH value. After completion of the reaction, the reaction solution was adjusted to pH of 6.5 to 7.0 by addition of 10% aqueous phosphoric acid and the acetone was removed by distillation at room temperature under a reduced pressure, following by addition of 1 kg of sodium chloride and by adjustment of the pH to 2.0 by addition of a 10% phosphoric acid solution. Thereafter, the resultant mixture was extracted with 1.5 l, 1 l and 1 l portions of n-butanol.

The n-butanol extract containing the cephem compound was in turn extracted three times with 0.6 l portions of a 0.2 M phosphorate buffer solution (at a pH 6.5). The aqueous phase of the phosphate buffer solution was washed with 0.5 l of ethyl acetate and was saturated with sodium chloride, followed by adjustment of the pH value to 2.0 by addition of a 10% phosphoric acid solution and by three extractions with 0.5 l, 0.3 l and 0.3 l portions of ethyl acetate.

The resultant extract containing the cephem compound in ethyl acetate was washed with a sodium chloride-saturated solution and dried over anhydrous magnesium sulfate, followed by removal of the solvent by distillation under a reduced pressure. Treatment of the resultant residue with petroleum ether gave 40.2 g of crude N-(2-phenoxyethoxycarbonyl) cephalosporin C (64% purity). The recovery yield of the cephem derivative was 92.3% in terms of the cephalosporin C content in the starting fermentation broth filtrate.

10 g of the crude cephalosporin C derivative was treated in the same manner as in Example 1 to give 6.1 g of N-(2-phenoxyethoxycarbonyl) cephalosporin C (94% purity).

A silica gel thin-layer chromatogram (determined using a 1:2 mixture of acetone and methanol as a developing solvent) gave a spot of N-(2-phenoxyethoxycarbonyl) cephalosporin C at $R_f$ 0.69.

The above process was repeated using magnesium sulfate as the salting-out agent to give a recovery yield of 90.7% in terms of the cephalosporin C content in the starting fermentation broth filtrate.

This cephalosporin C derivative had the following characteristic properties:
 Melting Point: 97° to 100° C (decomposed)
 Ultraviolet Absorption Spectrum: $\lambda_{max}^{methanol} = 264$ m$\mu$ and 270 m$\mu$
 Infra-red Absorption Spectrum (Disk Methods using KBr): 1790 cm$^{-1}$
 Elementary Analysis: Calculated for $C_{25}H_{29}N_3O_{11}S$: C, 51.80%; H, 5.05%; N, 7.25%. Found: C, 51.61%; H, 5.20%; N, 6.95%.

EXAMPLE 6

One liter of the fermentation broth filtrate containing 2,000 $\gamma$/ml of cephalosporin C which was obtained in Example 1 was employed and adjusted to pH of 2.0 by addition of hydrochloric acid and well washed with 200 ml of ethyl acetate to remove the fatty matter. The washed broth filtrate was then adjusted to pH of 8.0 to 8.5 by addition of aqueous sodium hydroxide and then was added with a solution of 4 g of 2-n-butoxyethoxycarbonyl chloride in 40 ml of dry acetone at 15° to 25° over about 20 minutes under stirring. During the dropwise addition of the chloride reagent, the reaction mixture was maintained at a pH of 8 – 8.5 by occasional addition of 5N aqueous sodium hydroxide. The mixture was agitated for further 30 minutes at 15°– 25° C at the same pH value as mentioned above.

After the completion of the reaction, the reaction solution was adjusted to pH 6.0 by addition of 5N hydrochloric acid and then passed through a column of 200 ml of an anion-exchange resin ("Amberlite" IRA-68 of acetate form) to make the cephem product adsorbed by the resin. The resin column was washed with 1 l of water and then developed with an aqueous 0.5M sodium chloride-hydrochloric acid solution at pH 3.0, so that the N-(2-n-butoxyethoxycarbonyl) cephalosporin C was eluted out of the resin column. Such fractions of the eluate containing the desired cephem product were combined together (500 ml) and the solution was adjusted to pH of 2.0 and extracted twice with 300 ml portions of ethyl acetate to give an extract solution of the cephem product in ethyl acetate, which was, in turn, extracted with 300 ml of water at pH 5.5. The resulting aqueous solution was freeze-dried to give 4.3 g of a crude powder of N-(2-n-butoxyethoxycarbonyl) cephalosporin C (56% purity). In this case, the recovery yield amounted to 89.4% based on the cephalosporin C content in the fermentation broth filtrate employed.

EXAMPLE 7

A fermentation broth containing cephalosporin C was adjusted to pH of 6 to 7 and the cells were removed by filtration. The resulting filtrate contained 2000 γ/ml of cephalosporin C.

10 l of the filrate was well washed three times with 3 l portions of ethyl acetate to remove a fatty matter therefrom. 1 l of acetone was added to the washed filtrate, to which was further added a 20% sodium hydrogen phosphate solution or an 1N sodium hydroxide solution to adjust the pH to 8 to 8.5. Thereafter, to the resultant solution was dropwise added with agitation a solution of 27 g of 2-bromoethoxycarbonyl chloride in 0.5 l of dry acetone, at a temperature of 10° to 20° C over about 2 hours while maintaining the pH at 8 to 8.5 by adding thereto a 20% sodium hydrogen phosphate solution. After completion of the addition, the reaction mixture was continuously agitated at the same temperature at the same pH value for 1 hour.

After completion of the reaction, the pH of the reaction solution was adjusted to 6.5 to 7.0 by addition of a 10% phosphoric acid solution and the acetone was removed from the solution by distillation at room temperature under reduced pressure, followed by addition of 1 kg of sodium chloride and by adjustment of the pH to 2.0 by addition of a 10% phosphoric acid solution. The resultant solution was extracted with 1.5 l, 1 l and 1 l portions of n-butanol. The thus obtained n-butanol extract was further extracted with three times by means of 0.6 l portions of a 0.2 M phosphate buffer solution (at a pH of 6.5). Then the phosphate buffer solution containing the cephem derivative was washed with 0.5 l of ethyl acetate and the aqueous layer was made acidic (pH 2.0) by addition of a 10% phosphoric acid solution and saturated with sodium chloride, followed by extraction with 0.5 l, 0.3 l and 0.3 l portions of ethyl acetate at pH 2.0. The resultant extract in ethyl acetate was washed with 0.5 l of an aqueous sodium chloride-saturated solution and dried over anhydrous magnesium sulfate, followed by removal of the solvent by distillation. To the resultant residue was added petroleum ether to obtain 38 g of crude 2-bromoethoxycarbonyl cephalosporin C (63% purity). The recovery yield of the cephem derivative was 92% in terms of the cephalosporin C content in the fermentation broth filtrate.

10 g of the crude cephem product which contained 63% of the cephalosporin C component was dissolved in 100 ml of water and saturated with sodium chloride, followed by adjustment of the pH to 2.0 by addition of a 10% phosphoric acid solution. The resultant solution was extracted three times with 50 ml portions of ethyl acetate. The ethyl acetate extract was in turn extracted three times with 20 ml portions of a 0.2 M phosphate buffer solution (having a pH of 6.5). The resultant extract in the phosphate buffer solution was saturated with sodium chloride and was adjusted to pH 2.0 by addition of a 10% phosphoric acid solution. The thus treated extract solution was further extracted three times with 50 ml portions of ethyl acetate. The resultant ethyl acetate extract solution was washed with 50 ml of a sodium chloride-saturated aqueous solution and dried over anhydrous magnesium sulfate, followed by removal of the solvent by distillation under reduced pressure. To the resultant residue was added a mixture of ether and petroleum ether to precipitate 5.8 g of N-(2-bromoethoxycarbonyl) cephalosporin C (95% purity).

A silica gel thin-layer chromatogram which was determined using a 3:2 mixture of ethyl acetate and methanol as the developing solvent showed at $R_f$ of 0.51 a spot of N-(2-bromoethoxycarbonyl) cephalosporin C.

The cephalosporin C derivative could be purified through a silica gel chromatography (using a 1:3 mixture of methanol and ethyl acetate as the developing solvent).

This cephalosporin C derivative had the following characteristic properties:

Melting Point: 83° to 85° C (with decomposition)
Ultraviolet Absorption Spectrum: $\lambda_{max}^{methanol} = 262$ m$\mu$ and $\epsilon = 7500$
Infra-red Absorption Spectrum (in KBr disk): 1790 cm$^{-1}$
Elementary Analysis:
Calculated for $C_{19}H_{24}N_3O_{10}SBr$: C, 40.29%, H, 4.27%, N, 7.42%. Found: C, 40.21%; H, 4.56%, N, 7.40%.

EXAMPLE 8

The pH of a cephalosporin C-containing fermentation broth was adjusted to 6 to 7 and the cell were filtered out. The resultant filtrate contained 2000 γ/ml of cephalosporin C.

10 l of the filtrate was washed three times with 1 l portions of ethyl acetate to remove the fatty materials therefrom. To the resultant washed aqueous phase was added 3 l of acetone and a suitable amount of an 1N sodium hydroxide solution to adjust the pH to 8 to 8.5. To the aqueous solution was further dropwise added with agitation a solution of 20.6 g of 2-chloroethoxycarbonyl chloride in 0.5 l of dry acetone, at a temperature of 10° to 20° C over about 2 hours while maintaining the pH at 8 to 8.5 by addition of aqueous 1N sodium hydroxide. The reaction mixture was continuously agitated for further 1 hour at a temperature of 10° to 20° C at a pH of 8 to 8.5. Then, the reaction solution was reduced to pH of 6.5 to 7.0 by addition of a 10% phosphoric acid solution and distilled at room temperature under reduced pressure to remove the acetone. To the resultant concentrated solution was added 1 kg of sodium chloride and a 10% phosphoric acid solution to adjust the pH to 2. The solution was then extracted with 1.5 l, 1 l and 1 l portions of n-butanol. The extract solution in n-butanol was, in turn, subjected to extraction three times with 0.6 l portions of a 0.2 M phosphate buffer solution (having a pH value of 6.5). The resultant aqueous extract (the buffer solution) was washed with 0.5 l of ethyl acetate, mixed with a 10% phosphoric acid solution to adjust the pH to 2.0, and it was then saturated with sodium chloride, followed by extraction with 0.5 l, 0.3 l and 0.3 l portions of ethyl acetate. The resultant extract solution in ethyl acetate was washed with an aqueous sodium chloride-saturated solution and dried over anhydrous magnesium sulfate, followed by removal of the solvent from the solution under reduced pressure. To the resultant residue was added petroleum ether to give 35 g of crude

cephalosporin C (68.6% purity).

The recovery yield of the cephalosporin derivative was 95% in terms of the cephalosporin C content in the broth filtrate.

10 g of the crude product which contained 68.6% of the cephalosporin C derivative was treated in the same manner as in Example 1 to afford 6.6 g of a purified N-(2-chloroethoxycarbonyl) cephalosporin C (97% purity).

The silica gel thin-layer chromatogram which was obtained using a solvent system of 3:2 ethyl acetate-methanol showed a spot of N-(2-chloroethoxycarbonyl) cephalosporin C at $R_f$ 0.50.

The cephalosporin C derivative could be purified through a silica gel chlomatography (using as a developing solvent a 1:3 mixture of methanol and ethyl acetate).

This cephalosporin C derivative had the following characteristic properties:

Melting Point: 104° to 108° C (with decomposition)
Ultraviolet Absorption Spectrum: $\lambda_{max}^{methanol} = 261$ m$\mu$ and $\epsilon = 7500$
Infra-red Absorption Spectrum (in KBr disk): 1790 cm$^{-1}$
Elementary Analysis:
Calculated for $C_{19}H_{24}N_3O_{10}SCl$: C, 43.72%; H, 4.63%; N, 8.05%.
Found: C, 43.51%; H, 4.52%; N, 7.92%.

EXAMPLE 9

10 l of the filtrate which was obtained in Example 1 was washed three times with 3 l portions of ethyl acetate to remove the fatty matter therefrom. The washed filtrate was admixed with 1 l of acetone and a 20% sodium hydrogenphosphate solution or an 1N sodium hydroxide solution to adjust the pH to 8 to 8.5. To the thus treated filrate was dropwise added with agitation a solution of 22.6 g of 3-chloropropoxycarbonyl chloride in 0.5 l of dry acetone, at a temperature of 10° to 20° C over about 2 hours while maintaining the pH at 8 to 8.5 by addition of a 20% sodium hydrogen-phosphate solution. The reaction mixture was further continuously agitated for 1 hour at a temperature of 10° to 20° C at a pH of 8 to 8.5. After completion of the reaction, the reaction solution was adjusted to pH 6.5 to 7.0 by addition of a 10% phosphoric acid and distilled at room temperature under a reduced pressure to remove the acetone. The concentrated solution was added with 1 kg of sodium chloride and a 10% phosphoric acid to adjust the pH to 2.0, followed by extraction with 1.5 l, 1 l and 1 l portions of n-butanol. The resultant extract as the n-butanol solution was extracted with three 0.6 l portions of a 0.2 M phosphate buffer solution (having a pH of 6.5). The resultant extract (the buffer solution) was washed with 0.1 l of ethyl acetate and saturated with dosium chloride, followed by addition of a 10% phosphoric acid solution to adjust the pH to 2.0. Then, the solution was extracted with 0.5 l, 0.3 l and 0.3 l portions of ethyl acetate, respectively. The resultant ethyl acetate extract was washed with 0.5 l of a sodium chloride-saturated solution and dried over anhydrous magnesium sulfate. Thereafter, the extract was distilled under reduced pressure to remove the ethyl acetate. To the resultant concentrate was added petroleum ether to deposit 36 g of crude N-(3-chloropropoxycarbonyl) cephalosporin C (60.7% purity). The recovery yield was 85% in terms of the cephalosporin C content in the fermentation broth filtrate.

10 g of the crude product which contained 60.9% of the cephalosporin C derivative was purified in the same manner as in Example 1 to give 5.6 g of purified N-(3-chloropropoxycarbonyl) cephalosporin C (96% purity).

The silica gel thin-layer chromatogram which was determined using a solvent system of 3:2 ethyl acetatemethanol showed a spot of N-(3-chloropropoxycarbonyl) cephalosporin C at $R_f$ 0.49.

The cephalosporin C derivative could be further purified through a silica gel chromatography (using as a developing solvent a 1:3 mixture of methanol and ethyl acetate).

The purified cephalosporin C derivative had the following characteristics:
Melting Point: 100° – 101° C (with decomposition)
Ultraviolet Absorption Spectrum: $\lambda_{max}^{methanol} = 261$ m$\mu$ and $\epsilon = 7450$
Infra-red Absorption Spectrum (in KBr disk): 1790 cm$^{-1}$
Elementary Analysis:
Calculated for $C_{20}H_{26}N_3O_{10}SCl$: C, 44.82%; H, 4.89%; N, 7.84%.
Found: C, 44.54%; H, 4.92%; N, 7.76%.

EXAMPLE 10

10 l of the filrate which was obtained in Example 1 was washed three times with 3 l portions of ethyl acetate. To the washed filtrate were added 1 l of acetone and an 1N sodium hydroxide solution to adjust the pH to 8 to 8.5. To the solution was dropwise added with agitation a solution of 28 g of 2,3-dichloropropoxycarbonyl chloride in 0.5 l of dry acetone, at a temperature of 10° to 20° C over about 2 hours, while maintaining the pH at 8 to 8.5 by addition of an 1N sodium hydroxide solution. The reaction mixture was further continuously agitated for 1 hour at a temperature of 10° to 20° C at a pH of 8 to 8.5. After completion of the reaction, the reaction solution was adjusted to pH 6.5 to 7.0 by addition of a 10% phosphoric acid solution and distilled at room temperature under reduced pressure. Then, the concentrated solution so obtained was admixed with 1 kg of sodium chloride and a 10% phosphoric acid solution to adjust the pH to 2.0. The resultant mixture was extracted with 1.5 l, 1 l and 1 l portions of n-butanol. The resultant n-butanol extract solution was further extracted three times with each 0.6 l portions of a 0.2 M phosphate buffer solution (having a pH of 6.5). The extract (the buffer solution) was washed with 0.5 l of ethyl acetate, followed by saturation with sodium chloride and by adjustment of the pH to 2.0. The resultant mixture was subjected three times to extraction with 0.5 l, 0.3 l and 0.3 l portions of ethyl acetate.

The resultant extract as the ethyl acetate solution of the cephem derivative was washed with a sodium chloride-saturated aqueous solution and dried over anhydrous magnesium sulfate, followed by removal of the solvent by distillation under reduced pressure. To the resultant residue was added petroleum ether to give 38.0 g of crude N-2,3-dichloropropoxycarbonyl) cephalosporin C (62% purity). The recovery yield of the cephalosporin C derivative was 86.9% in terms of the cephalosporin C content in the fermentation broth filtrate.

10 g of the crude product which contained 62% of the cephalosporin C derivative was treated in the same manner as in Example 1 to yield 5.8 g of a purified N-(2,3-dichloropropoxycarbonyl) cephalosporin C (96.5% purity).

The silica gel thin-layer chromatogram which was obtained using a solvent system of 3:2 ethyl acetate-methanol showed a spot of N-(2,3-dichloropropoxycarbonyl) cephalsporin C at $R_f$ 0.51.

The cephalosporin C derivative could be further purified through a silica gel chromatography (using as a developing solvent a 1:3 mixture of methanol and ethyl ether).

This purified cephalosporin C derivative had the following characteristic properties:
Melting Point: 90° to 91° C (with decomposition)
Ultraviolet Absorption Spectrum: $\lambda_{max}^{methanol} = 262$ m$\mu$ and $\epsilon = 7500$
Infra-red Absorption Spectrum (in KBr disk): 1790 cm$^{-1}$
Elementary Analysis:
Calculated for $C_{20}H_{25}N_3O_{10}SCl_2$: C, 42.11%; H, 4.42%; N, 7.37%.
Found: C, 42.42%; H, 4.61%; N, 7.15%.

EXAMPLE 11

10 l of the filtrate which was obtained in the same manner as in Example 1 was treated three times with 3 l portions of ethyl acetate to remove the fatty matter. The washed filtrate was admixed with 1 l of acetone and then an 1N sodium hydroxide solution to adjust the pH to 8 to 8.5. Thereafter, a solution of 28 g of 1-chloromethyl-2-chloroethoxycarbonyl chloride in 0.5 l of acetone was dropwise added thereto over about 2 hours while agitating at a temperature of 10° to 20° C, during which the pH was maintained at 8 to 8.5. The mixture was continuously agitated for further 1 hour at the temperature at a pH of 8 to 8.5, followed by adding a 10% phosphoric acid solution to adjust the pH to 6.5 to 7.0. Then, the mixture was distilled at room temperature under a reduced pressure to remove the acetone and then 1 kg of sodium chloride was added to the concentrated solution, to which was further added a 10% phosphoric acid solution to adjust the pH to 2.0. The resultant mixture was extracted with 1.5 l, 1 l and 1 l portions of n-butanol. The resultant extract in n-butanol was, in turn, extracted three times with 0.6 l portions with 0.6 l of a 0.2 M phosphate buffer solution (having a pH of 6.5). Then aqueous extract as washed with 0.5 l of ethyl acetate and the water layer was then saturated with sodium chloride, followed by addition of a 10% phosphoric acid solution to adjust the pH to 2.0 and then by extraction of the reaction product using 0.5 l, 0.3 l and 0.3 l portions of ethyl acetate.

The resultant extract in ethyl acetate was washed with 0.5 l of a sodium chloride-saturated solution and dried over anhydrous magnesium sulfate, followed by removal of the solvent under a reduced pressure. To the resultant residue was added petroleum ether to give 36 g of crude N-(1-chloromethyl-2-chloroethoxycarbonyl) cephalosporin C (82.2% purity). The yield was 82.2% in terms of the cephalosporin C content in the starting fermentation broth filtrate. of the cephalosporin C derivative was treated in the same manner as in Example 1 to obtain 5.9 g of purified N-(1-chloromethyl-2-chloroethyoxycarbonyl) cephalosporin C (96% purity).

The silica gel thin-layer chromatogram which was obtained using a solvent system of 3:2 ethyl acetate-methanol showed a spot of N-(1-chloromethyl-2-chloroethoxycarbonyl) cephalosporin C at $R_f$ 0.51.

The cephalosporin C derivative could be purified through a silica gel chromatography (using as a developing agent a 1:3 mixture of methanol and ethyl acetate).

This purified cephalosporin C derivative had the following characteristic properties:
Melting Point: 95° to 96° C (decomposed)
Ultraviolet Absorption Spectrum: $\lambda_{max}^{methanol} = 262$ m$\mu$ and $\epsilon = 7500$
Infra-red Absorption Spectrum (in KBr): 1790 cm$^{-1}$
Elementary Analysis:
Calculated for $C_{20}H_{25}N_3O_{10}SCl_2$: C, 42.11% H, 4.42%; N, 7.37%.
Found: C, 42.05%; H, 4.50%; N, 7.21%.

EXAMPLE 12

20 g of N-(2-chloroethoxycarbonyl) cephalosporin C which was obtained in Example 8 and 5.6 g of 2-mercapto-5-methyl-1,3,4-thiadiazole were introduced into 300 ml of water and intereacted at a temperature of 60° to 65° C for 6.5 hours, during which the pH of the reaction solution was maintained at 5.5 to 6.5 by addition of aqueous sodium bicarbonate. The reaction solution was admixed with 2 l of acetone and allowed to stand at 0° C overnight to precipitate an oily material. The oily material was separated from the solution and admixed with 800 ml of acetone for precipitation, followed by filtration and washing with acetone to give 16.6 g of a disodium salt of 7-[5-(2-chloroethoxycarbamido)adipinamido]-3-(5-methyl-1,3,4-thiadiazole-2-ylthiomethyl)-3-cephem-4-carboxylic acid.

This cephem compound had the following properties:
Decomposition Point: above 170° C
Ultraviolet Absorption Spectrum: $\lambda_{max}^{H_2O} = 269$ m$\mu$ ($E_1^{1\%}{}_{cm} = 157$)

EXAMPLE 13

The process of Example 12 was repeated using 4.88 g of 5-mercapto-1-methyl-1H-tetrazole instead of 2-mercapto-5-methyl-1,3,4-thiadiazole, thereby to give 18.2 g of a disodium salt of 7-[5-(2-chloroethoxycarbamido)adipinamido]-3-(1-methyl-1H-tetrazole-5-ylthiomethyl)-3-cephem-4-carboxylic acid.

This cephem compound had the following properties:
Decomposition Point: above 130° C
Ultraviolet Asborption Spectrum: $\lambda_{max}^{H_2O} = 263$ to 265 m$\mu$ ($E_1^{1\%}{}_{cm} = 118$)

EXAMPLE 14

20 g of N-(2-chloroethoxycarbonyl) cephalosporin C and 4.88 g of 5-mercapto-2-methyl-1,3,4oxadiazole were dissolved in 250 ml of water and treated in the same manner as in Example 12 to give 15.45 g of disodium salt of 7-[5-(2-chloroethoxycarbamido)adipinamido]-3-(2-methyl-1,3,4-oxadiazole-5-ylthiomethyl)-3-cephem-4-carboxylic acid.

This cephem compound had the following properties:
Decomposition Point: Decomposed gradually above 140° C Ultraviolet Absorption Spectrum: $\lambda_{max}^{H_2O} = 257$ to 259 m$\mu$ ($E_1^{1\%}{}_{cm} = 158$)

EXAMPLE 15

5.60 g of N-[2-n-butoxyethoxycarbonyl] cephalosporin C was suspended in 30 ml of methylene chloride, to which were added 2.22 g of triethylamine and 4.72 g of N,N-dimethylaniline. Then, 5.43 g of trimethylchlorosilane was slowly added into the mixture, followed by agitation for reaction at 0° to 5° C for 1 hour. To the reaction solution was added 2.70 g of phosphorus pentachloride for further reaction at a temperature of −40° to −30° C for 1 hour and then −20° to −10° C for 1 hour. Then, 12.7 ml of absolute methanol was added to the reaction solution, which was agitated at −20° to −10° C for 2 hours and allowed to stand in a freezer of −20° C overnight. Furthermore, 6.53 g of N,N-dimethylaniline was added to the reaction solution, into which was further dropwise added a mixture of 25 ml of methylene chloride and 1.93 g of 2-thienylacetyll chloride over 1 hour while maintaining at −30° to −20° C. The mixture was further agitated at the above reaction temperature for 2.5 hours, followed by addition of 40 ml of ice water and then a 10% sodium hydrogen carbonate to adjust the pH to 2.0. The resultant mixture was further agitated for 30 min and the reaction mixture was allowed to stand, so that the organic layer was separated from the aqueous phase of the reaction mixture. The organic layer isolated was added with 40 ml of water and then was aqueous 10% sodium hydrogen carbonate under agitation to adjust the pH to 7.5. Then, an aqueous layer was separated from said organic layer and was admixed with ethyl acetate and 2N hydrochloric acid to adjust the pH to 2.0, followed by separation of the ethyl acetate layer from the aqueous layer. The ethyl acetate solution thus separated was washed with water, dried over anhydrous magnesium sulfate and distilled in vacuo to remove the ethyl acetate.

Ether was added to the resultant oily residue to deposit 3.16 g of 7-(2-thienylacetoamido)-3-acetoxymethyl-3-cephem-4-carboxylic acid.

This cephem derivative had the following properties:
Decomposition Point: 154° to 157° C
Ultraviolet Absorption Spectrum: $\lambda_{max} = 234$ m$\mu$ ($E_1$ $_{cm}^{1\%} = 15300$) and $= 260$ m$\mu$ ($E_1$ $_{cm}^{1\%} = 2470$)

EXAMPLE 16

6.04 g of N-[2-(n-butoxyethoxy)ethoxycarbonyl] cephalosporin C was suspended in 30 ml of methylene chloride, to which were added 2.22 g of triethylamine and 4.72 g of N,N-dimethylaniline. Then, 8.05 g of dimethoxydichlorosilane was dropwise introduced into the resultant solution while agitating at 0° to 5° C for 1 hour. To the reaction solution was added 2.70 g of phosphorus pentachloride for reaction at a temperature of −40° C to −30° C for 1 hour and at a temperature of −20° to −10° C for 1 hour. 26.5 ml of absolute n-butanol was added to the reaction solution, followed by agitation at −20° to −10° C for 2 hours. The resultant solution was allowed to stand overnight. Thereafter, 6.53 g of N,N-dimethylaniline was added to the solution, into which was dropwise added over 1 hour 30 ml of a mixture of a methylene chloride and 2.26 g of 4-pyridylmercaptoacetyl chloride while maintaining the reaction temperature at −30° to −20° C. Then, the reaction solution was agitated at the reaction temperature for 2.5 hours, followed by addition of 50 ml of ice water and then 10% aqueous sodium hydrogen carbonate to adjust the pH to 2.0. The resultant solution was agitated for 20 min. and was adjusted to pH 3.0 and treated in the same manner as in Example 15 to give 3.22 g of 7-(α-4-pyridylthioacetoamido)-3-acetoxymethyl-3-cephem-4-carboxylic acid.

The cephem derivative obtained had the following properties:
Decomposition Point: 142 to 145° C
Ultraviolet Absorption Spectrum: $\lambda_{max} = 260$ m$\mu$ ($E_1$ $_{cm}^{1\%} = 386$)

EXAMPLE 17

5.60 g of N-(2-n-butoxyethoxycarbonyl) cephalosporin C was suspended in 35 ml of dichloroethane, to which were added 2.22 g of triethylamine and 4.72 g of N,N-dimethylaniline and further added dropwise 7.82 g of trimethoxychlorosilane while agitating at a temperature of 0° to 5° C for 1 hour. The reaction solution was admixed with 2.70 g of phosphrous pentachloride and stirred at a temperature of −40° to −30° C for 1 hour and then at −20° to −10° C for 1 hour. Thereafter, 26.4 ml of absolute n-butanol was added to the reaction solution, which was agitated at −20° C for 2 hours and allowed to stand at −20° C overnight. The resultant solution was further admixed with 6.53 g of N,N-dimethylaniline to which was then dropwise added at −30° to −20° C over 70 min. a solution of 1.25 g of cyanoacetyl chloride in 25 ml of methylene chloride. The resultant solution was agitated at −30° to −20° C for further 3 hours, to which was then added 40 ml of ice water and adjusted to pH 2.0 by addition of aqueous 10% sodium hydrogen carbonate. The mixture obtained was agitated for 20 min. Thereafter, the organic layer was separated from the reaction mixture and admixed with 30 ml of ethyl acetate and then with aqueous 10% sodium hydrogen carbonate solution to adjust the pH to 7.0. An aqueous layer was separated from the organic layer and admixed with 50 ml of ethyl acetate and then 2N HCl to adjust the pH to 2.0. Thereafter, the ethyl acetate layer was separated from the aqueous layer of the resultant admixture. The ethyl acetate solution thus separated was washed with water and dried over anhydrous magnesium sulfate, followed by removal of the ethyl acetate by distillation under reduced pressure. Ether was added to the resultant oily residue to give 2.17 g of 7-cyanoacetamido-3-acetoxymethyl-3-cephem-4-carboxylic acid.

The cephem derivative thus obtained had the following properties:
Decomposition Point: 168° to 170° C
Ultraviolet Absorption Spectrum: $\lambda_{max} = 260$ m$\mu$ ($E_1$ $_{cm}^{1\%} = 9300$)

EXAMPLE 18

5.60 g of N-(2-n-butoxyethoxycarbonyl) cephalosporin C was suspended in 30 ml of methylene chloride, to which were added 2.22 g of triethylamine and 4.72 g of N,N-dimethylaniline. To the mixture was slowly dropwise added 6.32 g of 2-chloro-1,3,2-dioxaphospholane under ice-cooling while agitating at 0° to 5° C for 1 hour. The reaction mixture was admixed with 6.25 g of phosphorus pentachloride and agitated at a temperature of −40° to −30° C for 1 hour and then at −20° to −10° C for 1 hour. To the reaction mixture was further added 12.7 ml of absolute methanol, followed by agitation at −20° to −10° C for 2 hours. The mixture so obtained was allowed to stand in a freezer of −20° C overnight. Then 6.53 g of N,N-dimethylaniline was introduced into the reaction mixture, into which was dropwise added a solution of 1.93 g of 2-thienylacetyl chloride in 25 ml of methylene chloride at −30° to −20° over 1 hour. Thereafter, the admixture was agitated at −30° to −20° C for further 2.5 hours, followed by addition of 40 ml of ice water and then aqueous 10% sodium hydrogen carbonate to adjust the pH to 2.0. The mixture so obtained was further agitated for 30 min.

Then, the mixture was left to separate into the organic layer and aqueous phases the organic solvent layer was separated and added with 40 ml of water, and then with aqueous 10% sodium hydrogen carbonate to adjust the pH to 7.5. The aqueous layer of the resultant admixture was separated and admixed with ethyl acetate and then 2N HCl to adjust the pH to 2.0, followed by separation of the ethyl acetate layer. The ethyl acetate solution thus separated was washed with water and dried over magnesium sulfate and then distilled in vacuo to effect the removal of the ethyl acetate. The resultant oily residue was mixed with ether to give 3.04 g of 7-(2-thienylacetoamido)-3-acetoxymethyl-3-cephem-4-carboxylic acid.

The cephem derivative had the following properties:
Decomposition Point: 154° to 157° C
Ultraviolet Absorption Spectrum: $\lambda_{max} = 234$ m$\mu$ ($E_1$ $_{cm}^{1\%} = 15300$), $= 260$ m$\mu$ ($E_1$ $_{cm}^{1\%} = 2470$)

EXAMPLE 19

6.04 g of N-(2-n-butoxyethoxyethoxycarbonyl) cephalosporin C was suspended in 30 ml of chloroform, to which were added 2.22 g of triethylamine and 4.72 g of N,N-dimethylaniline. To the mixture was slowly added dropwise 6.32 g of 2-chloro-1,3,2-dioxaphospholane under ice-cooling, followed by agitation at a temperature of −5° to 0° C for 1 hour. To the resultant reaction solution was added 6.25 g of phosphorus pentachloride, and the mixture was stirred at −40° to −30° C for 1 hour and then at −20° to 10° C for 1 hour. Further, 12.7 ml of absolute methanol was added to the reaction solution, which was then agitated at −20° to −10° C for 2 hours and allowed to stand overnight in a freezer of −20° C. Thereafter, 6.53 g of N,N-dimethylaniline was added to the reaction solution, into which was dropped 30 ml of a methylene chloride, containing 2.26 g of 4-pyridylmercaptoacetyl chloride, at −30° to −20° C over 1 hour. The resultant solution was agitated at −30° to −20° C for 2 hours, to which were added 50 ml of ice water and then aqueous 10% sodium hydrogen carbonate to adjust the pH to 2.0. The mixture was agitated for 20 min. and adjusted to pH 3.0. The organic solvent layer of the mixture was separated from the aqueous phase and treated in the same manner as in Example 18 to afford 3.4 g of 7-($\alpha$-4-pyridylthioacetoamido)-3-acetoxymethyl-3-cephem-4-carboxylic acid.

The cephem derivative had the following properties:
Melting Point: 143 to 146° C
Ultraviolet Absorption Spectrum: $\lambda_{max} = 260$ m$\mu$ ($E_1$ $_{cm}^{1\%} = 386$)

EXAMPLE 20

The process of Example 18 was repeated using cyanoacetyl chloride instead of 2-thienylacetyl chloride, thereby to produce 7-cyanoacetamido-3-acetoxymethyl-3-cephem-4-carboxylic acid. Yield 69.2%.

The cephem derivative thus obtained had the following properties:

Decomposition Point: 168 to 170° C
Ultraviolet Absorption Spectrum: $\lambda_{max} = 260$ m$\mu$ ($E_1$ $_{cm}^{1\%} = 9300$)

EXAMPLE 21

5.22 g of N-(2-chloroethoxycarbonyl) cephalosporin C was suspended in 30 ml of dichloroethane, to which were added 2.22 g of triethylamine and 2.54 g of N,N-dimethylaniline. To the mixture was added dropwise 2.58 g of dimethoxychlorosilane under ice-cooling, followed by agitation at −5° to 0° C for 1 hour. To the resultant reaction solution was added 270 g of phosphorus pentachloride at −50° C, followed by agitation at −40° to −30° C for 1 hour and then at −20° C to −10° C for 1 hour. Then, the agitated reaction solution was cooled to −50° C, to which were added a mixture of 26.5 ml of absolute n-butanol and 0.50 g of N,N-dimethylaniline. The resultant solution was agitated at −40° to −30° C for 1 hour and then at −20° to −10° C for 1 hour, and subsequently introduced into a mixed solution of 50 ml of ice water, 24 ml of methanol and 2 g of sodium formate, followed by agitation for 20 min. Thereafter, sodium formate was slowly added to the resultant solution to adjust the pH to 3.5. The admixture was allowed to stand at 0° C overnight to give a precipitate, which was then filtered and washed with 30 ml of water, 30 ml of methylene chloride, 30 ml of 50% aqueous acetone, and 30 ml of acetone in this order affording 2.56 g of 7-aminocephalosporanic acid (at a yield of 94.2%).

EXAMPLE 22

5.22 g of N-(2-chloroethoxycarbonyl) cephalosporin C was suspended in 30 ml of chloroform, to which were added 2.22 g of triethylamine and 2.54 g of N,N-dimethylaniline. Then, 2.50 g of trimethoxychlorosilane was dropped into the suspension under ice-cooling and then agitated at a temperature of −5° to 0° C for 1 hour. The resultant reaction solution was cooled to −50° C and added with 2.70 g of phosphorus pentachloride at a temperature of −40° to −30° C for 1 hour and then at −20° to −10° C for 1 hour. Thereafter, the solution was again cooled to −50° C and added with a mixture of 7 ml of absolute methanol and 0.4 g of N,N-dimethylaniline while agitating at −40° to −30° C for 1 hour and then at a temperature of −20° to −10° C for further 1 hour. The resultant reaction mixture was introduced into a mixed solution of 50 ml of ice water and 24 ml of methanol, to which was further added sodium formate to adjust the pH to 2.5, followed by agitation for 20 min. The agitated mixture was added with sodium formate to adjust the pH to 3.5, and it was allowed to stand at 0° C overnight for precipitation. The resultant crystal was filtered off and washed with 30 ml of water, 30 ml of chloroform, 30 ml of 50% aqueous acetone and 30 ml of acetone in this order, thereby to give 2.53 g of 7-aminocephalosporinic acid (yield 93%).

Similarly, the following results were obtained with the under-mentioned agents for protecting the carboxyl groups as well as the under-mentioned alcohol which reacted to form the iminoether.

| Protecting Agent for Carboxyl Groups | Alcohol | Yield |
| --- | --- | --- |
| Methoxytrichlorosilane | Methyl alcohol | 89.4% |
| Diethoxydichlorosilane | " | 87.5% |
| Trimethylchlorosilane | " | 90.2% |
| Triethylchlorosilane | n-Butylalcohol | 88.4% |

-continued

| Protecting Agent for Carboxyl Groups | Alcohol | Yield |
|---|---|---|
| Trimethoxychlorosilane | " | 93.2% |
| Phosgene | Propyleneglycol | 88.7% |
| Methoxycarbonylchloride | " | 87.6% |
| Methyldimethoxychlorosilane | Butylene glycol | 90.3% |
| Methyltrichlorosilane | Methyl alcohol | 88.4% |
| Methylmethoxydichlorosilane | " | 91.6% |

EXAMPLE 23

5.22 g of N-(2-chloroethoxycarbonyl) cephalosporin C was suspended in 30 ml of methylene chloride, to which was added 2.22 g of triethylamine and 2.54 g of N,N-dimethylaniline. To the resultant suspension was dropwise added 4.04 g of 2-chloro-1,3,2-dioxaphospholane, under ice-cooling, followed by agitation at a temperature of −5° to 0° C for 1 hour. To the reaction solution at −50° C was added 2.70 g of phosphorus pentachloride at −40° to −30° C for 1 hour and then at 20° to −10° C for further 1 hour. The resultant reaction solution was cooled to −50° C and added with a mixture of 7 ml of absolute methanol and 0.50 g of N,N-dimethylaniline and agitated for reaction at −40° to −30° C for 1 hour and then at −20° to −10° C for 1 hour. The agitated reaction mixture was introduced into a mixed solution of 50 ml of ice water and 24 ml of methanol and then added with 2 g of ammonium formate to adjust the ph to 3.5. Thereafter, the solution was allowed to stand at 0° C overnight to give a precipitate which was filtered and washed with 30 ml of water, 30 ml of methylene chloride, 30 ml of 50% aqueous acetone and 30 ml of acetone successively, thereby to produce 2.48 g of 7-amino-cephalosporanic acid (yield 91.2%).

Similarly, the following results were obtained with the under-mentioned protecting agents for carboxyl groups, and the under-mentioned alcohol which reacted to form the iminoether.

| Protecting Agent for Carboxyl Groups | Alcohol | Yield |
|---|---|---|
| Methoxydichlorophosphine | Methyl alcohol | 89.3% |
| Butoxydichlorophosphine | n-Butyl alcohol | 91.5% |
| Dimethoxychlorophosphine | Propyleneglycol | 93.2% |
| Dibutoxychlorophosphine | Butyleneglycol | 91.3% |
| 2-chloro-1,3,2-dioxaphosphorinane | Methyl alcohol | 88.4% |

EXAMPLE 24

5.22 g of N-(2-chloroethoxycarbonyl) cephalosporin C was suspended in 30 ml of chloroform, to which were added 2.22 g of triethylamine and 2.54 g of N,N-dimethylaniline. To the suspension was dropwise added 4.38 g of phosphorus trichloride under ice-cooling, followed by agitation at a temperature of −5° to 0° C for 1 hour. Then, 2.70 g of phosphorus pentachloride was added to the resultant reaction solution which was stirred, at −40° to −30° C for 1 hour and then at −20° to −10° C for 1 hour. The reaction solution was cooled to −50° C and added with a mixed solution of 40 ml of absolute propyleneglycol and 0.40 g of N,N-dimethylaniline while agitating at −40° to −30° C for 1 hour and then at of −20° to −10° C for 1 hour. The agitated mixture was introduced into a mixed solution of 50 ml of ice water and 20 ml of methanl to which was slowly added ammonium formate to adjust the pH to 2.0, followed by agitation for 20 min. and further addition of ammonium formate to adjust the pH to 3.5. The mixture was allowed to stand at 0° C overnight to give a precipiate which was filtered and washed with 30 ml of acetone, 30 ml of chloroform, 30 ml of 50% aqueous acetone and 30 ml of acetone in this order affording 2.61 g of 7-aminocephalosporanic acid. (yield 95.9%).

EXAMPLE 25

5.6 g of N-[2-(n-butoxy)ethoxycarbonyl] cephalosporin C was suspended in 50 ml of dichloroethane, to which was added 2.22 g of triethylamine and 4.72 g of N,N-dimethylaniline. To the suspension was added 6.32 g of 2-chloro-1,3,2-dioxapholane under cooling with water followed by agitation at a temperature of 0° to 5° C for 1 hour. To the resultant solution was added 6.25 g of phosphorus pentachloride at −60° C, followed by reaction at −40° to −30° C for 1 hour and then at −20° to −10° C for 1 hour. Then, the thus reacted solution was again cooled to −60° C, to which was added a mixture of 15 ml of absolute methanol and 1.0 g of N,N-dimethylaniline, which was agitated for reaction at −40° to −30° C for 1 hour and then at −20° to −10° C for 1 hour. The resultant reaction soluton was poured into a mixed solution of 50 ml of ice water and 20 ml of methanol and stirred for 30 minutes adjusting a pH value of 2.5 by ammonium formate and then added with ammonium formate to adjust the pH to 3.5. The reaction mixture was allowed to stand at 0° C overnight to give a precipitate, which was filtered and washed with 30 ml of water, 30 ml of methylene chloride, 30 ml of 50% aqueous acetone and 30 ml of acetone in this order, thereby giving 1.96 g of 7-aminocephalosporanic acid.

The product thus obtained was identified as 7-aminocephalosporanic acid by an NMR analysis and Infrared and Ultraviolet spectrum analysis.

EXAMPLE 26

6.04 g of N-(2-n-butoxyethoxyethoxycarbonyl) cephalosporin C was suspended in 50 ml of methylene chloride, to which were added 2.22 g of triethylamine and 4.72 g of N,N-dimethylaniline. To the resultant suspension was dropwise added under ice-cooling 6.32 g of 2-chloro-1,3,2-dioxaphospholane followed by agitation at a temperature of 0° to 5° C for 1 hour. The resultant reaction solution was admixed with 6.25 g of phosphorus pentachloride at −60° C and agitated at −40° to −30° C for 1 hour and then at −20° to −10° C for 1 hour. The reaction mixture was again cooled to −60° C and added with a mixture of 30 ml of absolute n-butanol and 1.0 g of N,N-dimethylaniline and the admixture was agitated at −40° to −30° C for 1 hour and then at a temperature of −20° to −10° C for further 1 hour. Thereafter, the reaction solution was poured into a mixed solution of 50 ml of ice water, 20 ml of methanol and 2.0 g of ammonium formate and added with a suitable amount of ammonium formate to adjust the pH to 2.5, followed by agitation for 20 min. and by further addition of ammonium formate to adjust the pH to 3.0. The admixture so obtained was allowed to stand at 0° C overnight to give a precipitate, which was filtered and washed with 30 ml of water, 30 ml of methylene chloride, 30 ml of 50% aqueous acetone and 30 ml of acetone in this order thereby to afford 1.80 g of 7-aminocephalosporanic acid.

EXAMPLE 27

5.60 g of N-(2-n-butoxyethoxycarbonyl) cephalosporin C was suspended in 30 ml of methylene chloride, to which were added 2.22 g of triethylamine and 4.72 g of N,N-dimethylaniline. Then, 5.43 g of trimethylchlorosilane was dropwise added into the suspension under ice-cooling, followed by agitation at a temperature of 0° to 5° C for 1 hour. The resultant solution was cooled to −50° C and added with 2.70 g of phosphorus pentachloride for reaction at −20° to −10° C for 1 hour and then at −20° to −10° C for 1 hour. The reaction mixture was again cooled to −50° C, admixed with a mixture of 7 ml of absolute methanol and 0.50 g of N,N-dimethylaniline and further stirred for reaction at −40° to −30° C for 1 hour and then at −20° to −10° C for 1 hour. The resultant reaction solution was introduced into a mixed solution of 50 ml of ice water and 20 ml of methanol and agitated at a pH of 2.5 for 20 min. to which was slowly added ammonium formate to adjust the pH to 3.0. The admixture so obtained was allowed to stand at 0° C overnight for precipitation. The precipitate was filtered and washed with 30 ml of water, 30 ml of methylene chloride, 20 ml of 50% aqueous acetone and 30 ml of acetone in this order to give 2.20 g of 7-aminocephalosporanic acid.

EXAMPLE 28

6.04 g of N-(2-n-butoxyethoxyethoxycarbonyl) cephalosporin C was suspended in 30 ml of methylene chloride, to which were added 2.22 g of trimethylamine and 2.54 g of N,N-dimethylamine. Then, 2.58 g of dimethoxydichlorosilane was dropwise added into the suspension under ice-cooling, followed by agitation at a temperature of 0° to 5° C for 1 hour. The resultant solution was cooled to −50° C, added with 2.70 g of phosphorus pentachloride and agitated for reaction at −40° to −30° C for 1 hour and then at −20° to −10° C for 1 hour. The reaction mixture was again cooled to −50° C, admixed with a mixture of 14 ml of absolute n-butanol and 0.50 g of N,N-dimethylaniline and then stirred at −40° to −30° C for 1 hour and then at −20° to −10° C for 1 hour. The resultant solution was introduced into a mixed solution of 50 ml of ice water, 20 ml of methanol and 2.0 g of sodium formate and agitated at a pH of 2 for 20 min., to which was further slowly added sodium formate to adjust the pH to 3.5. The admixture so obtained was allowed to stand at 0° C overnight for precipitation. The precipitate was filtered and washed with 30 ml of water, 30 ml of methylene chloride, 30 ml of 50% aqueous acetone and 30 ml of acetone in this order to afford 1.99 g of 7-aminocephalosporanic acid

EXAMPLE 29

16.6 g of the disodium salt of 7-[5-(2-chloroethoxycarbamido)adipinamido]-3-(5-methyl-1,3,4-thiadiazole-2-ylthiomethyl)-3-cephem-4-carboxylic acid which was obtained in Example 12 was dissolved in 200 ml of water, and the solution was added with 2N HCl under ice-cooling to adjust the pH to 2.0. The resultant solution was extracted with three times with each 120 ml aliquot of ethyl acetate. The resultants extracts were combined together, and washed with 60 ml of aqueous sodium chloride-saturated solution and dried over anhydrous magnesium sulfate. Thereafter, the ethyl acetate solution was distilled on a water bath at a temperature lower than 25° C to remove the solvent. The resulting oily material was admixed with ethyl ether for precipitation.

As a result, 13.4 g of the cephem derivative in the form of a free discarboxylic acid was obtained.

6.0 g of the free dicarboxylic acid product was mixed with 40 ml of dichloromethane and the resultant mixture was cooled to −5° C, to which were added 2.22 g of triethylamine and 2.60 g of N,N-dimethylaniline. Further, 4.04 g of 2-chloro-1,3,2-dioxaphospholane was dropwise added into the mixture, followed by agitation for reaction at −5° to 0° C for 1 hour. The reaction solution was cooled to −50° C, admixed with 2.70 g of phosphorus pentachloride and stirred at −40° to −30° C for 1 hour and then at −20° to −15° C. for 1.5 hours for reaction. The resultant reaction solution was again cooled to −50° C and added with a mixture of 12 ml of methanol and 0.4 g of N,N-dimethylaniline, and the admixture was stirred −40° to −30° C for 1 hour and then at −20° to −15° C for 1.5 hours. To the reaction solution was added a mixed solution of 50 ml of ice water, 25 ml of methanol and 2.0 g of ammonium formate with agitation, followed by adjustment of the pH to 0.9 to 1.1. to the resultant mixture was added ammonium formate to adjust the pH to 3.0. The admixture thus obtained was allowed to stand at 0° C overnight to give a crystalline product, which was then filtered and washed with water, dichloromethane and acetone in this order, affording 2.89 g of 7-amino-3-(5-methyl-1,3,4-thiadiazole-2-ylthiomethyl)-3-cephem-4-carboxylic acid.

The resultant compound had the following properties:

Decomposition Point: Gradually decomposed in the vicinity of 200° C.

Ultraviolet Absorption Spectrum: $\lambda_{max}^{H_2O} = 279$ m$\mu$ ($E_{1\ cm}^{1\%} = 390$)

Elementary Analysis: Calculated for $C_{11}H_{12}N_4O_3S_3$: C, 38.39%; H, 3.51%; N, 16.25%. Found: C, 38.06%; H, 3.68%; N, 15.95%.

EXAMPLE 30

18.2 g of disodium salt of 7-[5-(2-chloroethoxycarbamido)adipinamido]-3-(1-methyl-1H-tetrazole-5-ylthiomethyl)-3-cephem-4-carboxylic acid was dissolved in 220 ml of water, to which was added a suitable amount of 2N HCl to adjust the pH to 2.0. The resultant solution was subjected to extraction three times with 100 ml portions of ethyl acetate. The ethyl acetate extracts were combined together, and washed with 60 ml of a sodium chloride-saturated aqueous solution and dried over anhydrous magnesium sulfate. The, ethyl acetate was removed by distillation on a water bath of 25° C to give an oily material, to which was added ether for precipitation, affording 14.06 g of the cephem derivative in the form of a free dicarboxylic acid.

5.78 g of the dicarboxylic acid was introduced into 50 ml of dichloromethane and cooled to 5° C, to which were added 2.22 g of triethylamine and 2.7 g of N,N-dimethylaniline. Thereafter, 2.20 g of phosphorus trichloride was dropwise added into the solution, followed by agitation at a −5° to 0° C for 1 hour. The agitated solution was cooled to −50° C, added with 2.70 g of phosphorus pentachloride and stirred at −40° to −20° C for 1 hour and then at −20° to −15° C for further 1.5 hours for reaction. The reaction solution was again cooled to −50° C, admixed with a mixture of 30 ml of absolute n-butanol and 0.4 g of N,N-dimethylaniline and agitated at −40° to −30° C for 1 hour and then at −20° to −10° C for 1 hour. The resultant reaction solution was introduced into a mixed solution of 50 ml of ice water 25 ml of methanol and 2.0 g of sodium formate while agitating and continuously further agitated at a pH of 1.0 to 1.2 for 20 min, followed by addition of sodium formate to adjust the pH to 3.0. The mixture thus obtained was allowed to stand at 0° C overnight for precipitation. The resultant precipitate was filtered and washed with water, dichloromethane and acetone in this order to give 2.67 g of 7-amino-3-(1-methyl-1H-tetrazole-5-ylthiomethyl)-3-cephem-4-carboxylic acid.

The cephem derivative thus obtained had the following properties:

Decomposition Point: Decomposed slowly in the vicinity of 180° C.

Ultraviolet Absorption Spectrum: $\lambda_{max}^{H_2O} = 272$ m$\mu$ ($E_{1\ cm}^{1\%} = 299$)

Elementary Analysis:
Calculated for $C_{10}H_{12}N_6O_3S_2$: C, 36.60%; H, 3.68%; N, 25.60%. Found: C, 36.25%; H, 3.38%; N, 25.11%.

EXAMPLE 31

15 g of disodium salt of 7-[5-(2-chloroethoxycarbamido)adipinamido]-3-(2-methyl-1,3,4-oxadiazole-5-ylthiomethyl)-3-cephem-4-carboxylic acid was treated in the same manner as in Example 30 to yield 10.1 g of the cephem derivative in the form of the free dicarboxylic acid.

Then 5.82 g of the dicarboxylic acid was also treated in the same procedure as in Example 30 to produce 2.74 g of 7-amino-3-(2-methyl-1,3,4-oxadiazole-5-ylthiomethyl)-3-cephem-4-carboxylic acid (yield 83.5%).

The resultant cephem derivative had the following properties:

Decomposition Point: Decomposed slowly at about 195° C.

Ultraviolet Absorption Spectrum: $\lambda_{max}^{H_2O} = 267$ to 269 m$\mu$ ($E_{1\ cm}^{1\%} = 283$)

Infra-red Absorption Spectrum: 1799 cm$^{-1}$ ($\beta$-lactam) 1615 cm$^{-1}$ (Carboxylic acid)

EXAMPLE 32

16.6 g of disodium salt of 7-[5-(2-chloroethoxycarbamido)-adipinamido]-3-(5-methyl-1,3,4-thiadiazole-2-ylthiomethyl)-3-cephem-4-carboxylic acid was dissolved in 200 ml of water, to which was added 2N HCl under ice-cooling to adjust the pH to 2.0. The solution was extracted three times with 120 ml portions of ethyl acetate. The resultant ethyl acetate extracts were combined together and washed with 60 ml of a saturated aqueous sodium chloride solution and dried over anhydrous magnesium sulfate. Then, the ethyl acetate solution was distilled on a water bath at a temperature lower than 25° C to give an oily residue, to which was added ether for precipitation, yielding 13.4 g of the cephem derivative in the form of free dicarboxylic acid.

6.0 g of the free dicarboxylic acid was charged into 50 ml of dichloromethane, which was cooled to −5° C. To the cooled solution were added 2.30 g of triethylamine and 2.60 g of N,N-dimethylaniline, into which was dropwise added 3.50 g of trimehoxychlorosilane, followed by agitation at −5° to 0° C for 1 hour. The resultant solution was cooled to −50° C and added with 2.70 g of phosphorus pentachloride, and the mixture was stirred at −40° to 25° C for 1 hour and then at −20° to −15° C for 1.5 hours. The reaction solution was again cooled to −50° C, added with a mixture of 12 ml of methanol and 0.4 g of N,N-dimethylaniline and then subjected to further reaction at −40° to −30° C for 1 hour and then at −20° to −10° C for 1 hour. The resultant reaction solution was introduced with agitation into a mixed solution of 50 ml of ice water, 25 ml of methanol and 2.0 g of ammonium formate and further agitated at a pH of 1.1 to 1.2 for 20 min, followed by addition of ammonium formate to adjust the pH to 3.5. The mixture thus obtained was allowed to stand at 0° C overnight for precipitation. The resultant precipitate was filtered and washed with water, dichloromethane and acetone in this order to give 3.08 g of 7-amino-3-(5-methyl-1,3,4-thiadiazole-2-ylthiomethyl)-3-cephem-4-carboxylic acid. The cephem derivative thus obtained had the following properties:

Decomposition Point: Decomposed slowly in the vicinity of 200° C.

Ultraviolet Absorption Spectrum: $\lambda_{max}^{H_2O} = 279$ m$\mu$ ($E_{1\ cm}^{1\%} = 390$)

Elementary Analysis: Calculated for $C_{11}H_{12}N_4O_3S_3$: C, 38.39%; H, 3.51%; N, 16.25%. Found: C, 37.98%; H, 3.63%; N, 16.09%.

EXAMPLE 33

18.2 g of disodium salt of 7-[5-(2-chloroethoxycarbamido)adipinamido]-3-(1-methyl-1H-tetrazole-5-ylthiomethyl)-3-cephem-4-carboxylic acid was dissolved in 220 ml of water, to which was added a suitable amount of 2N HCl under ice-cooling to adjust the pH to 2.0. The resultant solution was extracted three times with each 100 ml portion of ethyl acetate. The resultant ethyl acetate extracts were combined together, washed with 60 ml of sodium chloride-saturated aqueous solution, and dried over anhydrous magnesium sulfate. Then, the ethyl acetate solution was distilled on a water bath at 25° C to remove the solvent, leaving an oily material, to which was added ether for precipitation to give 14.60 g of the free dicarboxylic acid.

5.78 g of the free dicarboxylic acid was introduced into 50 ml of dichloromethane and cooled to −5° C, to which were added 2.30 g of triethylamine and 2.70 g of N,N-dimethylaniline. Then, 2.50 g of trimethylchlorosilane was dropwise added to the solution, which was agitated at −5° to 0° C for 1 hour. The agitated solution was cooled to −50° C, added with 2.70 g of phosphorus pentachloride and stirred at −40° to −20° C for 1 hour and then at −20° to −15° C for 1.5 hours for reaction. The reaction solution was cooled to −50° C, admixed with a mixture of 45 ml of absolute n-butanol and 0.4 g of N,N-dimethylaniline and kept at −40° to −30° C for 1 hour and then at −20° to −10° C for 1 hour for reaction. The resultant reaction solution was poured into a mixed solution of 50 ml of ice water, 25 ml of methanol and 2.0 g of ammonium formate with agitation and continuously agitated for 20 min. at a pH of 1.0 to 1.2, to which was added a suitable amount of ammonium formate to adjust the pH to 3.0. The mixture thus obtained was allowed to stand at 0° C overnight for precipitation. The resultant precipitate was filtered and washed with water, dichloromethane and acetone in this order, to give 2.82 g of 7-amino-3-(1-methyl-1H-tetrazole-5-ylthiomethyl)-3-cephem-4-carboxylic acid.

The resultant carboxylic acid had the following properties:

Decomposition Point: Decomposed slowly in the vicinity of 180° C.

Ultraviolet Absorption Spectrum: $\lambda_{max}^{H_2O} = 272$ mµ ($E_{1\ cm}^{1\%} = 299$)

Elementary Analysis: Calculated for $C_{10}H_{12}N_6O_3S_2$: C, 36.60%; H, 3.68%; N, 25.60%. Found: C, 36.24%; H, 3.89%; N, 25.12%.

EXAMPLE 34

12.5 g of the disodium salt of 7-[5-(2-chloroethoxycarbamido)adipinamido]-3-(2-methyl-1,3,4-oxadiazole-5-ylthiomethyl)-3-cephem-4-carboxylic acid which was obtained in Example 14 was treated in the same manner as in Example 33 to give 10.1 g of its free dicarboxylic acid. 5.82 g of the free dicarboxylic acid was also treated in the same manner as in Example 33 to yield 2.61 g of 7-amino-3-(2-methyl-1,3,4-oxadiazole-5-ylthiomethyl)-3-cephem-4-carboxylic acid (yield 79.2%).

The resultant carboxylic acid had the following properties:

Decompositon Point: Melted and decomposed slowly in the vicinity of 195° C.

Ultraviolet Absorption Spectrum: $\lambda_{max}^{H_2O} = 267$ to 269 mµ ($E_{1\ cm}^{1\%} = 283$)

Infra-red Absorption Spectrum: 1799 cm$^{-1}$ (β-lactam) 1615 cm$^{-1}$ (Carboxylic acid)

EXAMPLE 35

20 g of N-(n-butoxy ethoxycarbonyl) cephalosporin C was reacted with 6.0 g of 2-mercapto-5-methyl-1,3,4-thiadiazole in the same manner as in Example 12 to produce 14.01 g of disodium salt of 7-[5-(n-butoxyethoxycarbamido(adipinamido]-3-(5-methyl-1,3,4-thiadiazole-2-ylthiomethyl)-3-cephem-4-carboxylic acid (yield 62%).

The resultant carboxylic acid had the following properties:

Decomposition Point: 153° to 160° C

Ultraviolet Absorption Spectrum: $\lambda_{max}^{H_2O} = 266$ to 268 mµ ($E_{1\ cm}^{1\%} = 146$)

Infra-red Absorption Spectrum: 1765 cm$^{-1}$ (β-lactam)

EXAMPLE 36

20 g of N-(n-butoxyethoxycarbonyl) cephalosporin C was reacted with 5.3 g of 5-mercapto-1-methyl-1H-tetrazole in the same manner as in Example 13 to give 18.77 g of disodium salt of 7-[(5-n-butoxyethoxycarbamido)adipinamido]-3-(1-methyl-1H-tetrazole-5-ylthiomethyl)-3-cephem-4-carboxylic acid (yield 85.9%).

The resultant disodium salt had the following properties:

Decomposition Point: 116° to 128° C

Ultraviolet Absorption Spectrum: $\lambda_{max}^{H_2O} = 267$ to 269 mµ ($E_{1\ cm}^{1\%} = 144$)

Infra-red Absorption Spectrum: 1766 cm$^{-1}$ (β-lactam)

EXAMPLE 37

20 g of N-(n-butoxyethoxycarbonyl) cephalosporin C was reacted with 5.3 g of 5-mercapto-2-methyl-1,3,4-oxidiazole in the same manner as in Example 14 to give 18.17 g of disodium salt of 7-[5-(n-butoxyethoxycarbamido)adipinamido]-3-(2-methyl-1,3,4-oxadiazole-2-ylthiomethyl)-3-cephem-4-carboxylic acid (yield 83.2%).

The disodium salt thus obtained had the following properties:

Decomposition Point: 113° to 125° C

Ultraviolet Absorption Spectrum: $\lambda_{max}^{H_2O} = 257$ to 259 mµ ($E_{1\ cm}^{1\%} = 164$)

Infra-red Absorption Spectrum: 1765 cm$^{-1}$ (β-lactam)

EXAMPLE 38

12.5 g of the disodium salt of 7-[5-(n-butoxyethoxycarbamido)adipinamido]-3-(5-methyl-1,3,4-thiadiazole-2-ylthiomethyl)-3-cephem-4-carboxylic acid which was obtained in Example 35 was treated in the same manner as in Example 29 to give 12.1 g of the free dicarboxylic acid.

6.30 g of this free carboxylic acid was then treated in the same manner as in Example 29 to yield 2.80 g of 7-amino-3-(5-methyl-1,3,4-thiadiazole-2-ylthiomethyl)-3-cephem-4-carboxylic acid (yield 81.4%).

The free carboxylic acid had the following properties:

Decomposition Point: Decomposed slowly in a vicinity of 200° C.

Ultraviolet Absorption Spectrum: $\lambda_{max}^{H_2O} = 279$ mµ ($E_{1\ cm}^{1\%} = 390$)

Infra-red Absorption Spectrum: 1797 cm$^{-1}$ (β-lactam) 1617 cm$^{-1}$ (carboxylic acid)

EXAMPLE 39

13.2 g of the disodium salt of 7-[5-(n-butoxyethoxycarbamido)adipinamido]-3-(1-methyl-1H-tetrazole-5-ylthiomethyl)-cephem-4-carboxylic acid was treated in the same manner as in Example 30 to give 11.7 g of the free dicarboxylic acid. Then, 5.66 g of this free carboxylic acid was then treated in the same manner as in Example 30 to yield 2.79 g of 7-amino-3-(1-methyl-1H-tetrazole-5-ylthiomethyl)-3-cephem-4-carboxylic acid (yield 85.1%).

The free carboxylic acid had the following properties:

Decomposition Point: Melted and decomposed in the vicinity of 180° C.

Ultraviolet Absorption Spectrum: $\lambda_{max}^{H_2O} = 272$ mµ ($E_{1\ cm}^{1\%} = 299$)

Infra-red Absorption Spectrum: 1795 cm$^{-1}$ (β-lactam) 1619 cm$^{-1}$ (carboxylic acid

EXAMPLE 40

13.2 g of the disodium salt of 7-[5-(n-butoxyethoxycarbamido)adipinamido]-3-(2-methyl-1,3,4-oxadiazole-2-ylthiomethyl)-3-cephem-4-carboxylic acid which was obtained in Example 37 was treated in the same manner as in Example 30 to yield 10.9 g of the free dicarboxylic acid. 6.56 g of this free dicarboxylic acid was then treated in the same manner as in Example 30 to give 2.64 g of 7-amino-3-(2-methyl-1,3,4-oxadiazole-2-ylthiomethyl)-3-cephem-4-carboxylic acid (yield 80.5%).

The free carboxylic acid thus obtained had the following properties:

Decomposition Point: Melted and decomposed slowly in the vicinity of 195° C.

Ultraviolet Absorption Spectrum: $\lambda_{max}^{H_2O} = 267$ to 269 mµ ($E_{1\ cm}^{1\%} = 283$)

Infra-red Absorption Spectrum: 1799 cm$^{-1}$ (β-lactam) 1615 cm$^{-1}$ (carboxylic acid)

EXAMPLE 41

13.5 g of the disodium salt of 7-[5-(n-butoxyethoxycarbamido)adipinamido]-3-(5-methyl-1,3,4-thiadiazole-2-ylthiomethyl)-3-cephem-4-carboxylic acid was treated in the same manner as in Example 32 to yield 12.1 g of its free dicarboxylic acid. Then, 6.56 g of this free dicarboxylic acid was also treated in the same manner as in Example 32 to give 2.72 g of 7-amino-3-(5-methyl-1,3,4-thiadiazole-2-ylthiomethyl)-3-cephem-4-carboxylic acid (yield 79.2%).

The carboxylic acid thus obtained had the following properties:

Decomposition Point: Decomposed slowly in the vicinity of 200° C

Ultraviolet Absorption Spectrum: $\lambda_{max}^{H_2O} = 279$ m$\mu$ ($E_{1\ cm}^{1\%} = 390$)

Infra-red Absorption Spectrum: 1797 cm$^{-1}$ ($\beta$-lactam) 1617 cm$^{-1}$ (Carboxylic Acid)

EXAMPLE 42

13.2 g of the disodium salt of 7-[5-(n-butoxyethoxycarbamido)adipinamido]-3-(1-methyl-1H-tetrazole-5-ylthiomethyl)-3-cephem-4-carboxylic acid was treated in the same manner as in Example 33 to yield 11.7 g of its free dicarboxylic acid. 6.56 g of this free acid was also treated in the same manner as in Example 33 to give 2.66 g of 7-amino-3-(1-methyl-1H-tetrazole-5-ylthiomethyl)-3-cephem-4-carboxylic acid (yield 81.2%).

The acid had the following properties:

Decomposition Point: Melted and decomposed slowly in the vicinity of 180° C

Ultraviolet Absorption Spectrum: $\lambda_{max}^{H_2O} = 272$ m$\mu$ ($E_{1\ cm}^{1\%} = 299$)

Infra-red Absorption Spectrum: 1795 cm$^{-1}$ ($\beta$-lactam) 1619 cm$^{-1}$ (Carboxylic Acid

EXAMPLE 43

13.2 g of disodium salt of 7-[5-(n-butoxyethoxycarbamido)adipinamido]-3-(5-methyl-1,3,4-oxadiazole-2-ylthiomethyl)-3-cephem-4-carboxylic acid ws treated in the same manner as in Example 33, affording 10.9 g of its free dicarboxylic acid. 6.56 g of this free dicarboxylic acid was also treated in the same manner as in Example 33 to give 2.78 g of 7-amino-3-(5-methyl-1,3,4-oxadiazole-2-ylthiomethyl)-3-cephem-4-carboxylic acid (yield 84.7%).

The carboxylic acid thus obtained had the following properties:

Decomposition Point: Melted and decomposed slowly in the vicinity of 195° C

Ultraviolet Absorption Spectrum: $\lambda_{max}^{H_2O} = 267$ to 269 m$\mu$ ($E_{1\ cm}^{1\%} = 283$)

Infra-red Absorption Spectrum: 1799 cm$^{-1}$ ($\beta$-lactam) 1615 cm$^{-1}$ (Carboxylic acid)

EXAMPLE 44

The disodium salt of N-(2-chloroethoxycarbonyl)cephalosporin C was treated with 2-mercaptopyridine-1-oxide in the same manner as in Example 12. The 7-[5-(2-chloroethoxycarbamido)adipinamido]-3-(pyridine-1-oxide-2-ylthiomethyl)-3-cephem-4-carboxylic acid obtained was treated in the same manner as in Example 30 to give 7-amino-3-(pyridine-1-oxide-2-ylthiomethyl)-3-cephem-4-carboxylic acid. (yield 83.6%)

The acid thus obtained had the following properties:

Decomposition Point: Melted and decomposed slowly in the vicinity of 120° C

Ultraviolet Absorption Spectrum: $\lambda_{max}^{H_2O} = 238^{265}$ m$\mu$ ($E_{1\ cm}^{1\%} = 397^{183}$)

EXAMPLE 45

The disodium salt of N-(2-chloroethoxycarbonyl)cephalosporin C was treated with 2-mercapto-1,3,4-thiadiazole in the same manner as in Example 12. The 7-[5-(2-chloroethoxycarboxamido)adipinamido]-3-(1,3,4-thiadiazol-2-ylthiomethyl)-3-cephem-4-carboxylic acid obtained was treated in the same manner as in Example 30 to give 7-amino-3-(1,3,4-thiadiazole-2-ylthiomethyl)-3-cephem-4-carboxylic acid. (yield 79.1%)

The acid thus obtained had the following properties:

Decomposition Point: Melted and decomposed slowly in the vicinity of 185° C.

Ultraviolet Absorption Spectrum: $\lambda_{max}^{H_2O} = 272$ m$\mu$ ($E_{1\ cm}^{1\%} = 325$)

Similarly, 7-[5-(2-chloroethoxycarbamido)adipinamido]-3-(1,3,4-thiadiazole-2-ylthiomethyl)-3-cephem-4-carboxylic acid was treated in the same manner as in Example 33, to give 7-amino-3-(1,3,4-thiadiazole-2-ylthiomethyl)-3-cephem-4-carboxylic acid. (yield of 82.5%).

EXAMPLE 46

The disodium salt of N-(2-chloroethoxycarbonyl cephalosporin C was treated with 2-mercapto-pyrimidine in the same manner as in Example 12. The 7-[5-(2-chloroethoxycarbamido(adipinamido]-3-(pyrimidine-2-ylthiomethyl)-3-cephem-4-carboxylic acid obtained was treated in the same manner as in Example 30 to give 7-amino-3-(pyrimidine-2-ylthiomethyl)-3-cephem-4-carboxylic acid (yield 79.5%).

The acid thus obtained had the following properties:

Decomposition Point: Melted and decomposed slowly in the vicinity of 210° C

Ultraviolet Absorption Spectrum: $\lambda_{max}^{H_2O} = 256$ m$\mu$ ($E_{1\ cm}^{1\%} = 510$)

Similarly 7-[5-(2-chloroethoxycarbamido)adipinamido]-3-(pyrimidine-2-ylthiomethyl)-3-cephem-4-carboxylic acid was treated in the same manner as in Example 33, to yield 7-amino-3-(pyrimidine-2-ylthiomethyl)-3-cephem-4-carboxylic acid (yield 83.8%).

EXAMPLE 47

The disodium salt of N-(2-chloroethoxycarbonyl) cephalosporin C was treated with 2-mercapto-thiazole in the same manner as in Example 12. The 7-[5-(2-chloroethoxycarbamido)adipinamido]-3-(thiazole-2-ylthiomethyl)-3-cephem-4-carboxylic acid obtained was treated in the same manner as in Example 30 to give 7-amino-3-(thiazole-2-ylthiomethyl)-3-cephem-4-carboxylic acid (yield 74.5%).

The acid thus obtained had the following properties:

Decomposition Point: Melted and decomposed slowly in the vicinity of 210° C.

Ultraviolet Absorption Spectrum: $\lambda_{max}^{H_2O} = 273$ m$\mu$ ($E_{1\ cm}^{1\%} = 355$)

Similarly 7-[5-(2-chloroethoxycarbamido)adipinamido]-3-(thiazole-2-ylthiomethyl)-3-cephem-4-carboxylic acid was treated in the same manner as in Example 33, to give 7-amino-3-(thiazole-2-ylthiomethyl)-3-cephem-4-carboxylic acid (yield of 80.1%).

EXAMPLE 48

The disodium salt of N-(2-chloroethoxycarbonyl) cephalosporin C was treated with 5-mercapto-2-methyl-1,3,4-triazole in the same manner as in Example 12. The 7-[5-(2-chloroethoxycarbamido)adipinamido]-3-(2-methyl-1,3,4-triazole-5-ylthiomethyl)-3-cephem-4-carboxylic acid obtained was treated in the same manner as in Example 30 to give 7-amino-3-(2-methyl-1,3,4-triazole-5-ylthiomethyl)-3-cephem-4-carboxylic acid (yield 82.6%).

The compound thus obtained had the following properties:

Decomposition Point: Melted and decomposed slowly in the vicinity of 214° C

Ultraviolet Absorption Spectrum: $\lambda_{max}^{H_2O} = 270$ m$\mu$ ($E_{1\ cm}^{1\%} = 309$)

Similarly 7-[5-(2-chloroethoxycarbamido)adipinamido]-3-(2-methyl-1,3,4-triazole-5-ylthiomethyl)-3-cephem-4-carboxylic acid was treated in the same manner as in Example 33, to give 7-amino-3-(2-methyl-1,3,4-triazole-5-ylthiomethyl)-3-cephem-4-carboxylic acid (yield 83.8%).

EXAMPLE 49

The disodium salt of N-(2-chloroethoxycarbonyl) cephalosporin C was treated with 2-mercapto-1,3,4-triazole in the same manner as in Example 12. The 7-[5-(2-chloroethoxycarbamido)adipinamido]-3-(1,3,4-triazole-2-ylthiomethyl)-3-cephem-4-carboxylic acid obtained was treated in the same manner as in Example 30 to give 7-amino-3-(1,3,4-triazole-2-ylthiomethyl)-3-cephem-4-carboxylic acid (yield 75.9%).

The acid thus obtained had the following properties:

Decomposition Point: Melted and decomposed slowly in the vicinity of 195° C

Ultraviolet Absorption Spectrum: $\lambda_{max}^{H_2O} = 269$ m$\mu$ ($E_{1\ cm}^{1\%} = 306$)

Similarly 7-[5-(2-chloroethoxycarbamido)adipinamido]-3-(1,3,4-triazole-2-ylthiomethyl)-3-cephem-4-carboxylic acid was treated in the same manner as in Example 33, to give 7-amino-3-(1,3,4-triazole-2-ylthiomethyl)-3-cephem-4-carboxylic acid (yield 78.4%).

EXAMPLE 50

The disodium salt of N-(2-chloroethoxycarbonyl) cephalosporin C was treated with 2-mercapto-1-methyl-1,3,4-triazole in the same manner as in Example 12. The 7-[5-(2-chloroethoxycarbamido)adipinamido]-3-(1-methyl-1,3,4-triazole-2-ylthiomethyl)-3-cephem-4-carboxylic acid obtained was treated in the same manner as in Example 30 to give 7-amino-3-(1-methyl-1,3,4-triazole-2-ylthiomethyl)-3-cephem-4-carboxylic acid (yield 73.8%).

The acid thus obtained had the following properties:

Decomposition Point: Melted and decomposed slowly in the vicinity of 192° C

Ultraviolet Absorption Spectrum: $\lambda_{max}^{H_2O} = 271$ m$\mu$ ($E_{1\ cm}^{1\%} = 272$)

Similarly 7-[5-(2-chloroethoxycarbamido)adipinamido]-3-(1-methyl-1,3,4-triazole-2-ylthiomethyl)-3-cephem-4-carboxylic acid was treated in the same manner as in Example 33, to give 7-amino-3-(1-methyl-1,3,4-triazole-2-ylthiomethyl)-3-cephem-4-carboxylic acid (yield 80.5%).

EXAMPLE 51

An aqueous solution containing the disodium salt of N-(2-chloroethoxycarbonyl) cephalosporin C together with 5 molar proportions of sodium azide was adjusted to pH 6.5 and then heated at 60° C for 15 hours. The 7-[5-(2-chloroethoxycarbamido)adipinamido]-3-azidomethyl-3-cephem-4-carboxylic acid obtained had the following properties;

Decomposition Point: Melted and decomposed slowly in the vicinity of 78° C

Ultraviolet Absorption Spectrum: $\lambda_{max}^{H_2O} = 259$ to 261 m$\mu$ ($E_{1\ cm}^{1\%} = 91$)

The product thus obtained was treated in the same manner as in Example 30 to produce 7-amino-3-azidomethyl-3-cephem-4-carboxylic acid of the following properties:

Decomposition Point: Melted and decomposed slowly in the vicinity of 219° C

Ultraviolet Absorption Spectrum: $\lambda_{max}^{H_2O} = 260$ m$\mu$ ($E_{1\ cm}^{1\%} = 234$)

Similarly 7-[5-(2-chloroethoxycarbamido)adipinamido]-3-azidomethyl-3-cephem-4-carboxylic acid was treated in the same manner as in Example 33 to produce 7-amino-3-azidomethyl-3-cephem-4-carboxylic acid (yield 74.1%).

EXAMPLE 52

5.22 g of N-(2-chloroethoxycarbonyl) cephalosporin C was treated in the same manner as in Example 17, and the resultant iminoether compound was reacted with D-α-carbamoyloxyphenylacetyl chloride to give 3.15 g of 7-(D-α-carbamoyloxyphenylacetamido)-3-acetoxymethyl-3-cephem-4-carboxylic acid.

Infra-red Spectrum: 1765 cm$^{-1}$ (β-lactam) 1735 cm$^{-1}$ (carbamoyloxy, acetoxy) 1685 cm$^{-1}$ (amide)

NMR Spectrum (ppm: D$_2$O): 5.05 (doublet, C$_6$ proton, J=4.5) 5.80 (doublet, C$_7$ proton, J=4.5).

What we claim is:

1. A cephem derivative of the formula

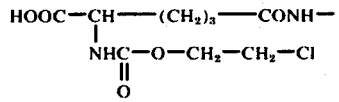
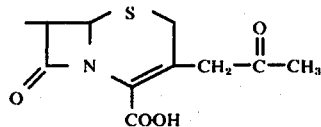

2. A cephem derivative of the formula

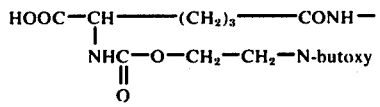
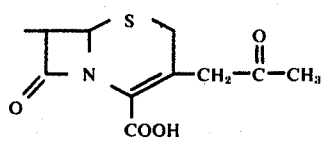

* * * * *